US012688797B2

(12) United States Patent
Egan et al.

(10) Patent No.: US 12,688,797 B2
(45) Date of Patent: Jul. 21, 2026

(54) SURGICAL TRAINER WITH MECHANICAL FEEDBACK

(71) Applicant: Texas Tech University System, Lubbock, TX (US)

(72) Inventors: Paul Egan, Lubbock, TX (US); Travis Reiss, Porter, TX (US); Kyle Fenn, Argyle, TX (US); Catherine A. Ronaghan, Lubbock, TX (US)

(73) Assignee: TEXAS TECH UNIVERSITY SYSTEM, Lubbock, TX (US)

( * ) Notice: Subject to any disclaimer, the term of this patent is extended or adjusted under 35 U.S.C. 154(b) by 187 days.

(21) Appl. No.: 18/715,423

(22) PCT Filed: Dec. 2, 2022

(86) PCT No.: PCT/US2022/051626
§ 371 (c)(1),
(2) Date: May 31, 2024

(87) PCT Pub. No.: WO2023/102168
PCT Pub. Date: Jun. 8, 2023

(65) Prior Publication Data
US 2025/0037610 A1      Jan. 30, 2025

Related U.S. Application Data

(60) Provisional application No. 63/285,465, filed on Dec. 2, 2021.

(51) Int. Cl.
*A61B 17/04* (2006.01)
*G09B 23/28* (2006.01)
*A61B 17/00* (2006.01)

(52) U.S. Cl.
CPC ............ *G09B 23/285* (2013.01); *A61B 17/04* (2013.01); *G09B 23/28* (2013.01); *A61B 2017/00707* (2013.01)

(58) Field of Classification Search
CPC ...... G09B 23/285; G09B 23/28; A61B 17/04; A61B 2017/00707
See application file for complete search history.

(56) References Cited

U.S. PATENT DOCUMENTS

| | | | | |
|---|---|---|---|---|
| 5,318,013 A | * | 6/1994 | Wilk | ................. A61B 17/0218 606/198 |
| 8,306,753 B2 | | 11/2012 | Cowley et al. | |
| 9,974,534 B2 | * | 5/2018 | Troxel | ................... A61B 17/04 |
| 11,452,514 B2 | * | 9/2022 | Truckey | ............. A61B 17/0206 |

(Continued)

OTHER PUBLICATIONS

PCT/US2022/051626. International Search Report and Written Opinion (Apr. 26, 2023).

*Primary Examiner* — Eddy Saint-Vil
(74) *Attorney, Agent, or Firm* — LOZA & LOZA, LLP; Kevin L. Soules

(57) ABSTRACT

A surgical training system, method, and apparatus comprise a biomaterial, a first clamp configured to engage the biomaterial and a second clamp configured to engage the biomaterial, at least one actuator operably connected to at least one of the first clamp and the second clamp wherein the at least one actuator is configured to impart tension in the biomaterial, and a patient body simulator arranged under the biomaterial.

13 Claims, 28 Drawing Sheets

(56)                   References Cited

U.S. PATENT DOCUMENTS

2007/0005108 A1*   1/2007   Simhon ................. A61B 17/11
                                                         606/216
2008/0064017 A1    3/2008   Grundmeyer, III et al.
2011/0190588 A1    8/2011   Mckay
2012/0205419 A1*   8/2012   Weir ................. A61B 17/0686
                                                         227/175.1
2016/0217710 A1    7/2016   Matonick et al.
2017/0011655 A1    1/2017   Sakezles et al.
2020/0294422 A1    9/2020   Hutmacher et al.
2021/0241655 A1    8/2021   Takeuchi et al.
2021/0338299 A1*  11/2021   El-Chafei ............. A61B 34/10
2022/0370138 A1*  11/2022   Shelton, IV ........... G09B 23/28

* cited by examiner

200

206

204 Device

205 External Device

202 Network

210

212

214

208 Storage

674

676

678

680

688

690

692

425

770

420

780

775

425

785

900

905   Start

910   Select training parameters

915   Configure biomaterial

920   Insert biomaterial edges in clamps

925   Clamp biomaterial

930   Apply tension to biomaterial

935   Create incision in biomaterial

940   Trainee sutures incision in biomaterial

945   Suturing completed

950   Additional tension applied to suture

955   Training completed

960   End

1400

1405

1410

1410

1410

1410

1405

1505

1600

1700

1710

1705

1715

1800

1805

1810

SURGICAL TRAINER WITH MECHANICAL FEEDBACK

CROSS REFERENCE TO RELATED APPLICATIONS

This patent application claims the priority and benefit under 35 U.S.C. § 119(e) of U.S. Provisional Patent Application Ser. No. 63/285,465 filed Dec. 2, 2021, entitled "SURGERY TRAINER." U.S. Provisional Patent Application Ser. No. 63/285,465 is herein incorporated by reference in its entirety.

TECHNICAL FIELD

Embodiments are generally related to the field of medical education. Embodiments are further related to the field of simulation. Embodiments are also related to anatomy. Embodiments are further related to surgery and surgical trainers. Embodiments are also related to suturing, suturing training, and testing devices. Embodiments are related to synthetic biomaterials. Embodiments are also related to surgical suture training devices with mechanical feedback. Embodiments are further related to a suture tester with mechanical feedback for training residents for abdominal wall closure surgery.

BACKGROUND

Surgery is complicated. As any medical student or resident can attest, there is a dramatic learning curve required to learn the skills required to complete a medical operation. Beyond the complexity of learning anatomy and physiology, surgical procedures also require a practiced hand in order to complete tasks including but not limited to suturing.

One exemplary procedure is known as a laparotomy. A laparotomy is a common surgical procedure involving an incision or multiple incisions in the abdominal wall in order to access the abdominal cavity. It can be difficult to learn exactly where to make incisions, how to avoid internal or external hazards, and how best to suture the incision to "close" the abdominal cavity when the procedure is complete.

Currently there are very few cost effective tools for practicing surgical procedures. Some current options include suture pads, human cadavers, pig abdominal walls, and synthetic biomaterial trainers. Each of these solutions have major drawbacks.

For example, suture pads are relatively inexpensive and simple but are not anatomically realistic. The pads are not under tension and therefore do not offer realistic stretching. On the other hand, cadavers offer excellent anatomical realism but are expensive and in short supply. A student cannot practice the same procedure multiple times on a cadaver, as is required to learn the nuances of a given technique.

Other prior art solutions include surgical simulations based in virtual or augmented reality. These options can be cost prohibitive and often fail to provide the haptic feedback required to truly internalize a given procedure.

Accordingly, there is a need in the art for cost effective and reusable systems and methods that recreate the physiological materials and forces experienced during surgery to help train surgeons as disclosed herein.

SUMMARY

The following summary is provided to facilitate an understanding of some of the innovative features unique to the embodiments disclosed and is not intended to be a full description. A full appreciation of the various aspects of the embodiments can be gained by taking the entire specification, claims, drawings, and abstract as a whole.

It is, therefore, one aspect of the disclosed embodiments to medical trainer.

It is another aspect of the disclosed embodiments to provide systems and apparatuses for surgical training.

It is another aspect of the disclosed embodiments to provide methods and systems for recreating physiological materials and forces experience during surgery.

It is another aspect of the disclosed embodiments to provide low cost high fidelity surgical training devices.

It will be appreciated that the methods and systems can be achieved according to the embodiments disclosed herein. For example, in an embodiment, a surgical trainer comprises a first clamp configured to engage a biomaterial, a second clamp configured to engage the biomaterial, and at least one actuator operably connected to at least one of the first clamp and the second clamp wherein the at least one actuator is configured to impart tension in the biomaterial. In an embodiment, the at least one actuator further comprises a first actuator operably connected to the first clamp and a second actuator operably connected to the second clamp. In an embodiment, the surgical trainer further comprises an articulating joint configured between the actuator and at least one of the first clamp and the second clamp, the articulating joint being configured to impart the tension in the biomaterial. In an embodiment, the surgical trainer further comprises an actuator controller configured to control the tension imparted on the biomaterial by the actuator operably connected to at least one of the first clamp and the second clamp. In an embodiment, the surgical trainer further comprises a patient body simulator arranged under the biomaterial. In an embodiment, the patient body simulator further comprises at least one of a synthetic body organ, a synthetic bone, and a synthetic bodily fluid. In an embodiment, the biomaterial comprises layers, the layers further comprising at least one of: synthetic skin, synthetic fat, synthetic fascia, and synthetic muscle. In an embodiment, each of the first clamp and the second clamp further comprise an upper bracket, at least one joining post formed in the upper bracket, a lower bracket, and at least one lower bracket guide hole configured to accept the at least one joining post. In an embodiment, the surgical trainer further comprises a lever configured on the upper bracket, the lever being adapted to connect the actuator to at least one of the first clamp and the second clamp. In an embodiment, the surgical trainer further comprises an imaging device, the imaging device configured to capture image data of the biomaterial. In an embodiment, the surgical trainer further comprises a computer system, said computer system comprising: at least one processor; and a computer-usable medium embodying computer program code, the computer-usable medium capable of communicating with the at least one processor, the computer program code comprising instructions executable by the at least one processor and configured for: accepting input of the image data from the imaging device and providing feedback associated with the image data of procedures performed on the biomaterial.

In an embodiment, a surgical training method comprises configuring a biomaterial, clamping the biomaterial with a first clamp, clamping the biomaterial with a second clamp, and imparting tension on the biomaterial with at least one actuator operably connected to at least one of the first clamp and the second clamp, wherein the biomaterial serves as a training medium for surgical procedures. In an embodiment of the method, the at least one actuator further comprises a first actuator operably connected to the first clamp and a second actuator operably connected to the second clamp. In an embodiment, the surgical training method further comprises configuring an articulating joint between the actuator and at least one of the first clamp and the second clamp, the articulating joint imparting the tension in the biomaterial. In an embodiment, the surgical training method further comprises controlling the tension imparted on the biomaterial with an actuator controller for the actuator operably connected to at least one of the first clamp and the second clamp. In an embodiment, the biomaterial comprises layers, the layers further comprising at least one of: synthetic skin, synthetic fat, synthetic fascia, and synthetic muscle. In an embodiment, the surgical training method further comprises capturing image data of the biomaterial with an imaging device. In an embodiment, the surgical training method further comprises accepting input of the image data from the imaging device and providing feedback associated with the image data of procedures performed on the biomaterial.

In another embodiment, a surgical training system comprises: a housing, a first slidable brace connected to a linear actuator, a second slidable brace connected to the linear actuator, a riser on each side of the first slidable brace, the riser comprising a cutout configured to accept a rod, and a riser on each side of the second slidable brace, the riser comprising a cutout configured to accept a rod. In an embodiment, the surgical training system further comprises a biomaterial and at least one rod configured to extend through the biomaterial.

BRIEF DESCRIPTION OF THE FIGURES

The accompanying figures, in which like reference numerals refer to identical or functionally similar elements throughout the separate views and which are incorporated in and form a part of the specification, further illustrate the embodiments and, together with the detailed description, serve to explain the embodiments disclosed herein.

DETAILED DESCRIPTION

Figure 1:
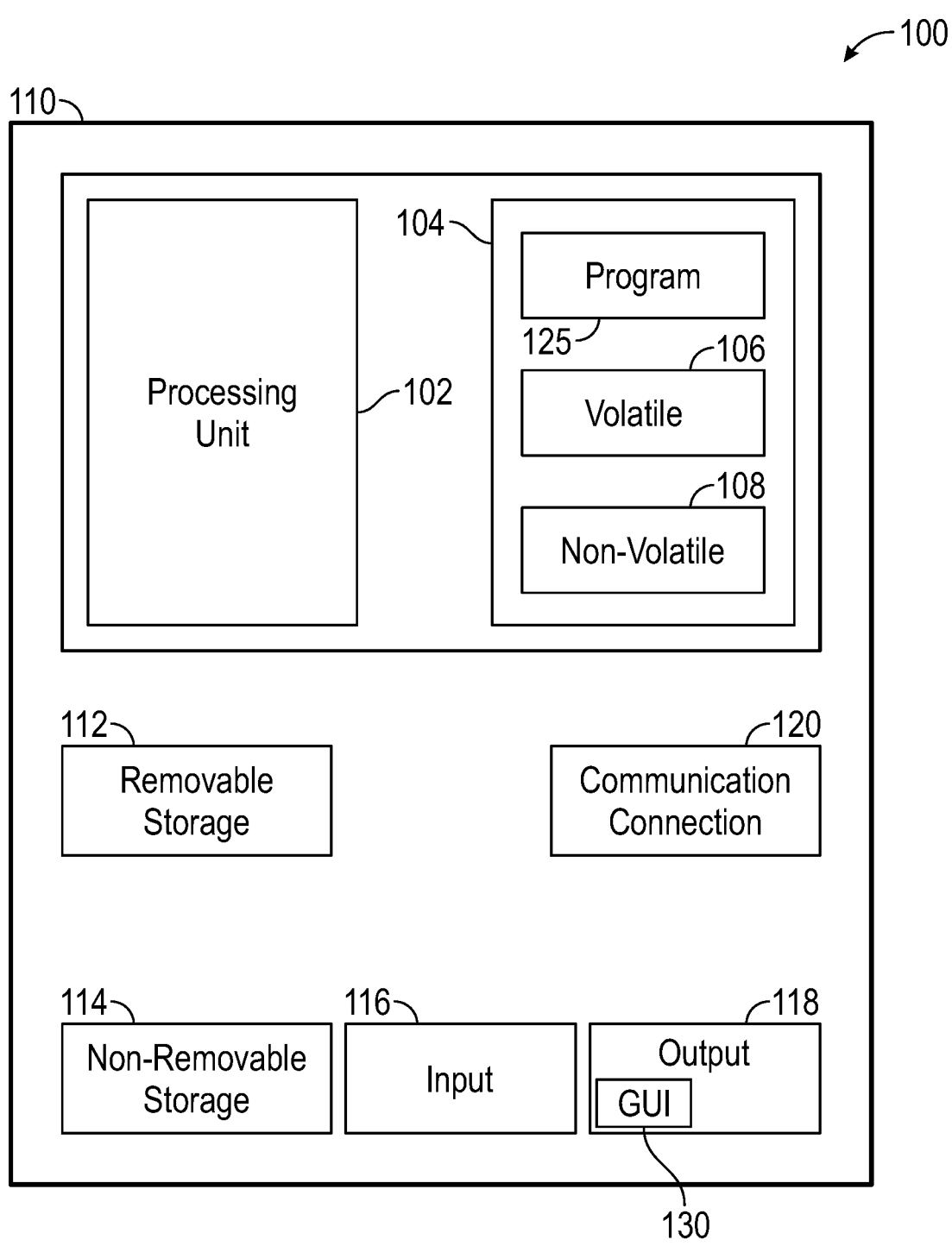
FIG. 1 depicts a block diagram of a computer system which is implemented in accordance with the disclosed embodiments.

Embodiments and aspects of the disclosed technology are presented herein. The particular embodiments and configurations discussed in the following non-limiting examples can be varied, and are provided to illustrate one or more embodiments, and are not intended to limit the scope thereof.

Reference to the accompanying drawings, in which illustrative embodiments are shown are provided herein. The embodiments disclosed can be embodied in many different forms and should not be construed as limited to the embodiments set forth herein; rather, these embodiments are provided so that this disclosure will be thorough and complete, and will fully convey the scope of the embodiments to those skilled in the art. Like numbers refer to like elements throughout.

The terminology used herein is for the purpose of describing particular embodiments only and is not intended to be limiting. As used herein, the singular forms "a", "an", and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Throughout the specification and claims, terms may have nuanced meanings suggested or implied in context beyond an explicitly stated meaning. Likewise, the phrase "in one embodiment" as used herein does not necessarily refer to the same embodiment and the phrase "in another embodiment" as used herein does not necessarily refer to a different embodiment. It is intended, for example, that claimed subject matter include combinations of example embodiments in whole or in part.

Unless otherwise defined, all terms (including technical and scientific terms) used herein have the same meaning as commonly understood by one of ordinary skill in the art. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCC, CBBAAA, CABABB, and so forth. The skilled artisan will understand that typically there is no limit on the number of items or terms in any combination, unless otherwise apparent from the context.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit, and scope of the invention. All such similar substitutes and modifications apparent to those skilled in the art are deemed to be within the spirit, scope and concept of the invention as defined by the appended claims.

Figure 2:
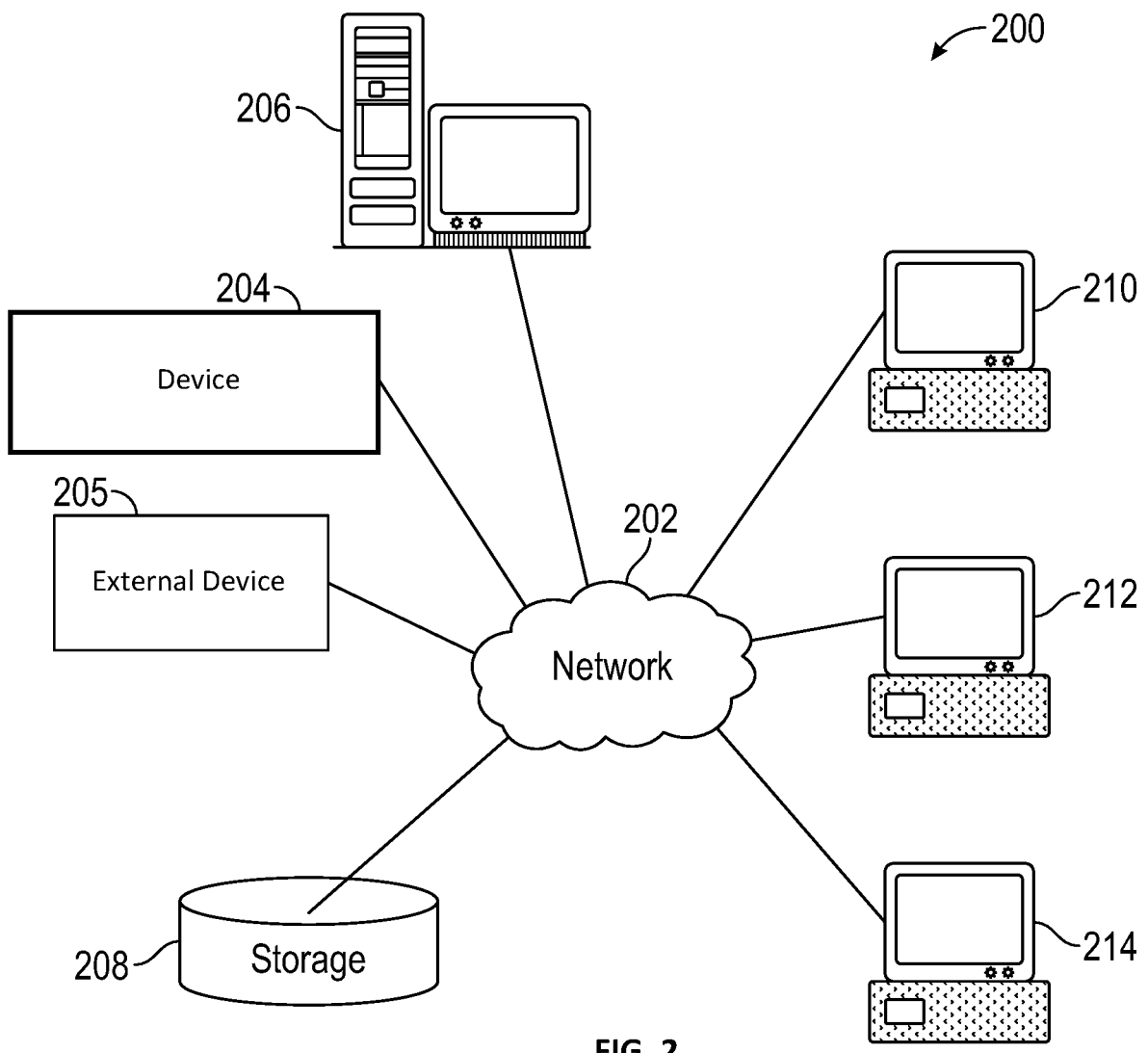
FIG. 2 depicts a graphical representation of a network of data-processing devices in which aspects of the present embodiments may be implemented.
Figure 3:
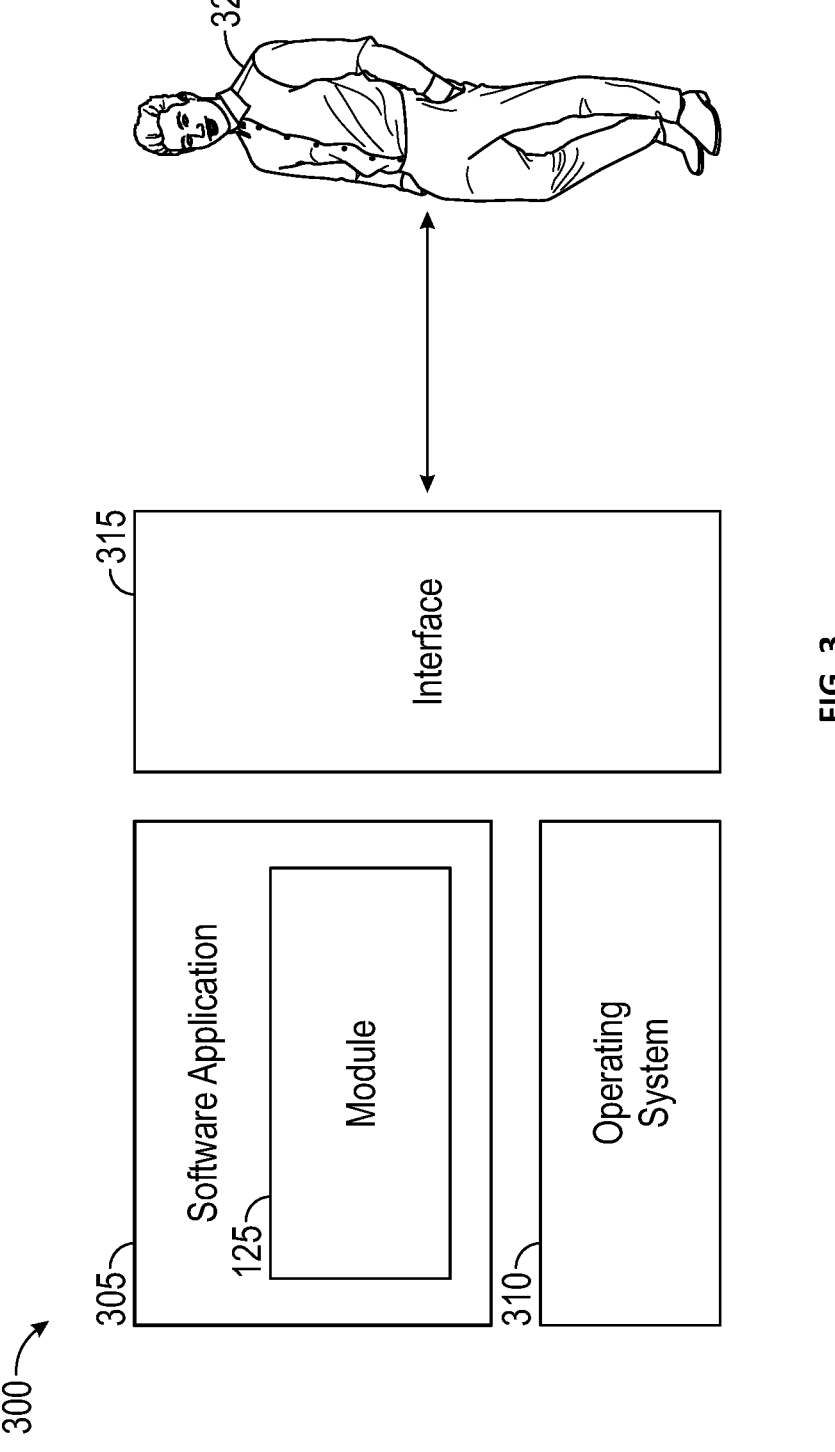
FIG. 3 depicts a computer software system for directing the operation of the data-processing system depicted in FIG. 1, in accordance with an example embodiment.

FIGS. 1-3 are provided as exemplary diagrams of data-processing environments in which embodiments may be implemented. It should be appreciated that FIGS. 1-3 are only exemplary and are not intended to assert or imply any limitation with regard to the environments in which aspects or embodiments of the disclosed embodiments may be implemented. Many modifications to the depicted environments may be made without departing from the spirit and scope of the disclosed embodiments.

A block diagram of a computer system 100 that executes programming for implementing parts of the methods and systems disclosed herein is provided in FIG. 1. A computing device in the form of a computer 110 configured to interface with controllers, peripheral devices, and other elements disclosed herein may include one or more processing units 102, memory 104, removable storage 112, and non-removable storage 114. Memory 104 may include volatile memory 106 and non-volatile memory 108. Computer 110 may include or have access to a computing environment that includes a variety of transitory and non-transitory computer-readable media such as volatile memory 106 and non-volatile memory 108, removable storage 112 and non-removable storage 114. Computer storage includes, for example, random access memory (RAM), read only memory (ROM), erasable programmable read-only memory (EPROM) and electrically erasable programmable read-only memory (EEPROM), flash memory or other memory technologies, compact disc read-only memory (CD ROM), Digital Versatile Disks (DVD) or other optical disk storage, magnetic cassettes, magnetic tape, magnetic disk storage, or other magnetic storage devices, or any other medium capable of storing computer-readable instructions, as well as data including image data.

Computer 110 may include, or have access to, a computing environment that includes input 116, output 118, and a communication connection 120. The computer may operate in a networked environment using a communication connection 120 to connect to one or more remote computers, remote sensors and/or controllers, detection devices, handheld devices, multi-function devices (MFDs), speakers, mobile devices, tablet devices, mobile phones, Smartphone, or other such devices. The remote computer may also include a personal computer (PC), server, router, network PC, RFID enabled device, a peer device or other common network node, or the like. The communication connection may include a Local Area Network (LAN), a Wide Area Network (WAN), Bluetooth connection, or other networks. This functionality is described more fully in the description associated with FIG. 2 below.

Output 118 is most commonly provided as a computer monitor, but may include any output device. Output 118 and/or input 116 may include a data collection apparatus associated with computer system 100. In addition, input 116, which commonly includes a computer keyboard and/or pointing device such as a computer mouse, computer track pad, or the like, allows a user to input instructions to computer system 100. A user interface can be provided using output 118 and input 116. Output 118 may function as a display for displaying data and information for a user, and for interactively displaying a graphical user interface (GUI) 130.

Note that the term "GUI" generally refers to a type of environment that represents programs, files, options, and so forth by means of graphically displayed icons, menus, and dialog boxes on a computer monitor screen. A user can interact with the GUI to select and activate such options by directly touching the screen and/or pointing and clicking with a user input device 116 such as, for example, a pointing device such as a mouse, and/or with a keyboard. A particular item can function in the same manner to the user in all applications because the GUI provides standard software routines (e.g., module 125) to handle these elements and report the user's actions. The GUI can further be used to display the electronic service image frames as discussed below.

Computer-readable instructions, for example, program module or node 125, which can be representative of other modules or nodes described herein, are stored on a computer-readable medium and are executable by the processing unit 102 of computer 110. Program module or node 125 may include a computer application. A hard drive, CD-ROM, RAM, Flash Memory, and a USB drive are just some examples of articles including a computer-readable medium.

FIG. 2 depicts a graphical representation of a network of data-processing systems 200 in which aspects of the present invention may be implemented. Network data-processing system 200 can be a network of computers or other such devices, such as mobile phones, smart phones, sensors, controllers, actuators, speakers, "internet of things" devices, and the like, in which embodiments of the present invention may be implemented. Note that the system 200 can be implemented in the context of a software module such as program module 125. The system 200 includes a network 202 in communication with one or more clients 210, 212, and 214. Network 202 may also be in communication with one or more devices 204, external devices 205 servers 206, and storage 208. Network 202 is a medium that can be used to provide communications links between various devices and computers connected together within a networked data processing system such as computer system 100. Network 202 may include connections such as wired communication links, wireless communication links of various types, and fiber optic cables. Network 202 can communicate with one or more servers 206, one or more external devices such as device 204, and a memory storage unit such as, for example, memory or database 208. It should be understood that device 204 may be embodied as a detector device, controller, receiver, transmitter, transceiver, transducer, driver, signal generator, testing apparatus, or other such device.

In the depicted example, device 204, server 206, and clients 210, 212, and 214 connect to network 202 along with storage unit 208. Clients 210, 212, and 214 may be, for example, personal computers or network computers, handheld devices, mobile devices, tablet devices, smart phones, personal digital assistants, controllers, recording devices, speakers, MFDs, etc. Computer system 100 depicted in FIG. 1 can be, for example, a client such as client 210 and/or 212 and/or 214.

Computer system 100 can also be implemented as a server such as server 206, depending upon design considerations. In the depicted example, server 206 provides data such as boot files, operating system images, applications, and application updates to clients 210, 212, and/or 214. Clients 210, 212, and 214 and device 204 are clients to server 206 in this example. Network data-processing system 200 may include additional servers, clients, and other devices not shown. Specifically, clients may connect to any member of a network of servers, which provide equivalent content.

In the depicted example, network data-processing system 200 is the Internet, with network 202 representing a worldwide collection of networks and gateways that use the Transmission Control Protocol/Internet Protocol (TCP/IP) suite of protocols to communicate with one another. At the heart of the Internet is a backbone of high-speed data communication lines between major nodes or host computers consisting of thousands of commercial, government, educational, and other computer systems that route data and messages. Of course, network data-processing system 200 may also be implemented as a number of different types of networks such as, for example, an intranet, a local area network (LAN), or a wide area network (WAN). FIGS. 1 and 2 are intended as examples and not as architectural limitations for different embodiments of the present invention.

FIG. 3 illustrates a software system 300, which may be employed for directing the operation of the data-processing systems such as computer system 100 depicted in FIG. 1. Software application 305, may be stored in memory 104, on removable storage 112, or on non-removable storage 114 shown in FIG. 1, and generally includes and/or is associated with a kernel or operating system 310 and a shell or interface 315. One or more application programs, such as module(s) or node(s) 125, may be "loaded" (i.e., transferred from removable storage 114 into the memory 104) for execution by the data-processing system 100. The data-processing system 100 can receive user commands and data through user interface 315, which can include input 116 and output 118, accessible by a user 320. These inputs may then be acted upon by the computer system 100 in accordance with instructions from operating system 310 and/or software application 305 and any software module(s) 125 thereof.

Generally, program modules (e.g., module 125) can include, but are not limited to, routines, subroutines, software applications, programs, objects, components, data structures, etc., that perform particular tasks or implement particular abstract data types and instructions. Moreover, those skilled in the art will appreciate that elements of the disclosed methods and systems may be practiced with other computer system configurations such as, for example, hand-held devices, mobile phones, smart phones, tablet devices multi-processor systems, microcontrollers, printers, copiers, fax machines, multi-function devices, data networks, micro-processor-based or programmable consumer electronics, networked personal computers, minicomputers, mainframe computers, servers, medical equipment, medical devices, and the like.

Note that the term "module" or "node" as utilized herein may refer to a collection of routines and data structures that perform a particular task or implements a particular abstract data type. Modules may be composed of two parts: an interface, which lists the constants, data types, variables, and routines that can be accessed by other modules or routines; and an implementation, which is typically private (accessible only to that module), and which includes source code that actually implements the routines in the module. The term module may also simply refer to an application such as a computer program designed to assist in the performance of a specific task such as word processing, accounting, inventory management, etc., or a hardware component designed to equivalently assist in the performance of a task.

The interface 315 (e.g., a graphical user interface 130) can serve to display results, whereupon a user 320 may supply additional inputs or terminate a particular session. In some embodiments, operating system 310 and GUI 130 can be implemented in the context of a "windows" system. It can be appreciated, of course, that other types of systems are possible. For example, rather than a traditional "windows" system, other operation systems such as, for example, a real-time operating system (RTOS) more commonly employed in wireless systems may also be employed with respect to operating system 310 and interface 315. The software application 305 can include, for example, module(s) 125, which can include instructions for carrying out steps or logical operations such as those shown and described herein.

The following description is presented with respect to embodiments of the present invention, which can be embodied in the context of, or require the use of, a data-processing system such as computer system 100, in conjunction with program module 125, and data-processing system 200 and network 202 depicted in FIGS. 1-3. The present invention, however, is not limited to any particular application or any particular environment. Instead, those skilled in the art will find that the system and method of the present invention may be advantageously applied to a variety of system and application software including database management systems, word processors, and the like. Moreover, the present invention may be embodied on a variety of different platforms including Windows, Macintosh, UNIX, LINUX, Android, Arduino, LabView and the like. Therefore, the descriptions of the exemplary embodiments, which follow, are for purposes of illustration and not considered a limitation.

Embodiments disclosed herein are directed to suture training/testing devices and systems primarily for medical education or other such applications. The disclosed embodiments comprise a suture tester with mechanical feedback for training students for abdominal wall closure surgery, or other such surgical procedures. The system can include an actuation assembly that applies mechanical tensile force Fa on a synthetic biomaterial. Embodiments can also include a physiological prototype that mimics the shape of a patient to provide additional physiological force.

In an exemplary embodiment, the device works by inserting a synthetic biomaterial representing, for example an abdominal wall, into a set of clamps that are connected by a joint to a set of actuators. The actuators are then initiated to pre-tension the material and pull it. The system can be arranged over a patient body simulator to further tension the biomaterial. A student can incise the biomaterial, conduct surgical procedures within the patient body simulator, and then complete suturing as if conducting a surgery with the synthetic biomaterial. After suturing is completed, the actuators exert further force to tension the sutures so the user can see how the sutures hold to mechanical loading conditions and determine their quality.

Figure 4A:
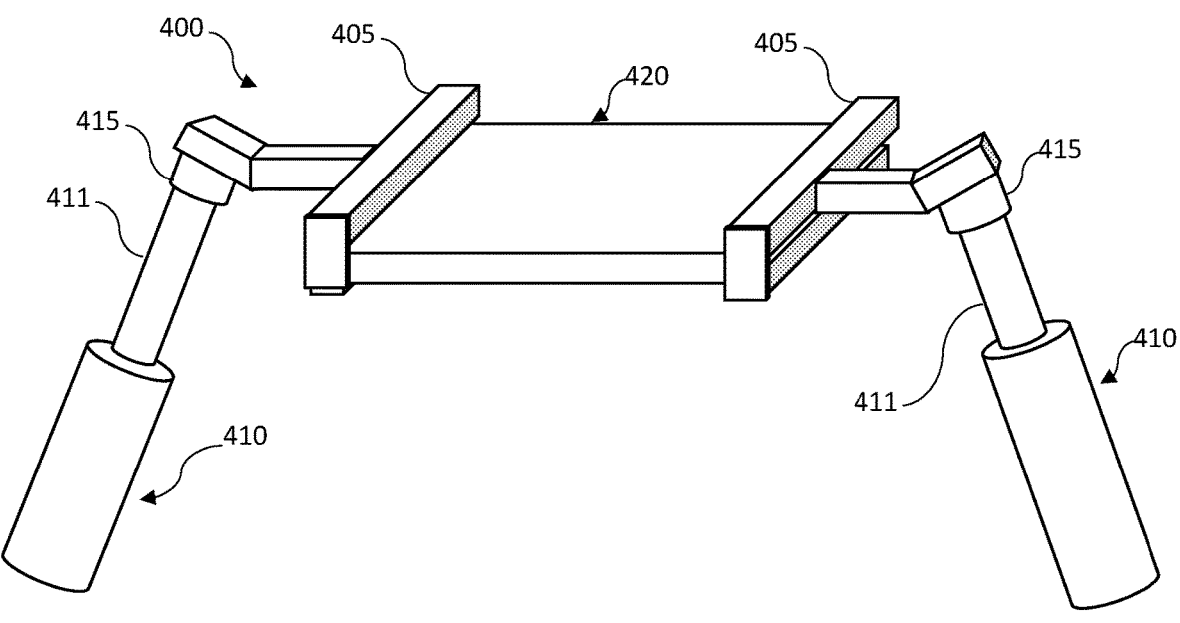
FIG. 4A depicts a surgical training system, in accordance with the disclosed embodiments.

FIG. 4A illustrates aspects of a surgical training system 400 in accordance with the disclosed embodiments. The system 400 generally comprises two clamps 405. Each of the clamps is operably mounted to an actuator 410 with a joint 415. The actuator can comprise an, electric, mechanical (screw), pneumatic, hydraulic, electromagnetic, or other such actuator configured to extend and retract the actuator arm 411. In other embodiments, bi-axial actuation can be provided. The clamps 405 each engage a side of a biomaterial 420, such that the biomaterial is stretched between the two clamps 405.

Figure 4B:
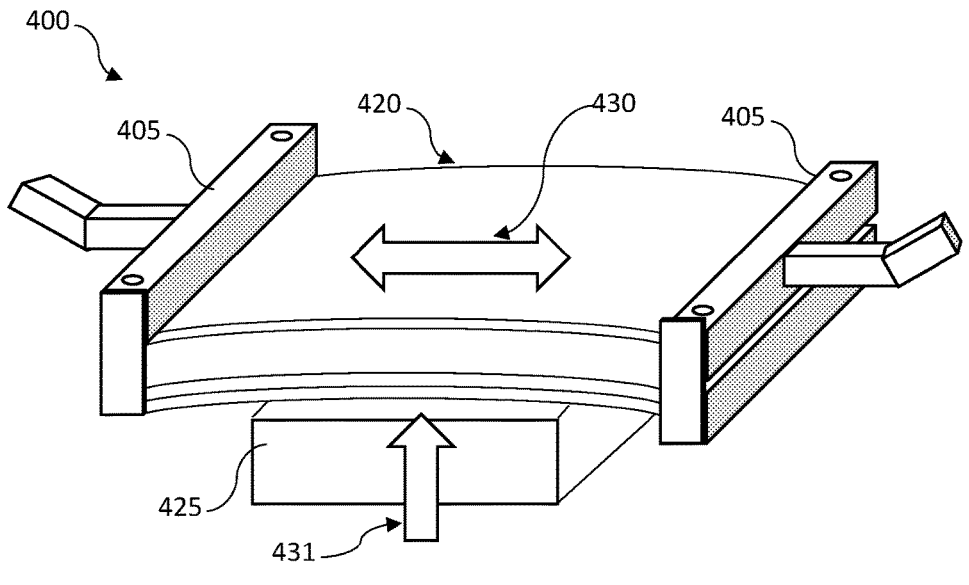
FIG. 4B depicts another view of a surgical training system, in accordance with the disclosed embodiments.

FIG. 4B illustrates the biomaterial 420 stretched by clamps 405 over a patient body simulator 425. It should be appreciated that the clamps can impart a force Fa 430 across the biomaterial 420, while the patient body simulator simultaneously imparts a force Fb 431 upwardly on the biomaterial 420. These forces are important as they replicate the tension forces a surgeon experiences when operating on a real human patient. The angle of actuators 410 and arms 411 relative to the biomaterial 420 can be changed to represent different curvatures of the body.

Figure 5A:
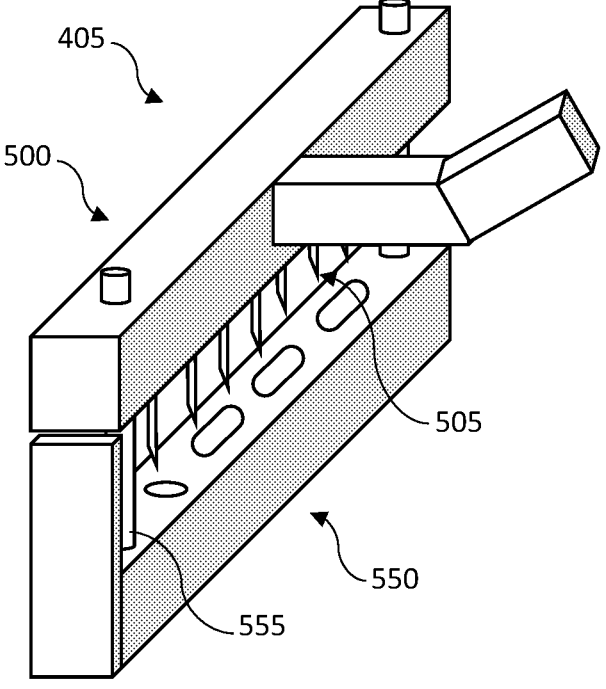
FIG. 5A depicts a clamp of a surgical training system, in accordance with the disclosed embodiments.

FIG. 5A illustrates aspects of the clamps 405. Each of the clamps 405 can comprise an upper bracket 500 and a lower bracket 550. The upper bracket 500 can further include array of at least one rivet 505. The lower bracket can include a guidepost 555 configured to properly align the upper bracket and lower bracket 550 as they are closed on the biomaterial 420. The guidepost 555 can comprise a structural cylinder of metal, plastic, polymer, or the like, installed in the lower bracket 550. A compliant hinge mechanism on the lower bracket 550 holds the clamps 405 together to create the clamping force. The purpose of the upper bracket 500 and lower bracket 550 is to clamp the biomaterial 420 in place so it is possible to apply a force on the clamp that is distributed evenly through the rivets 505 while testing the strength of sutures on the biomaterial 420 through tensile actuation.

Figure 5B:
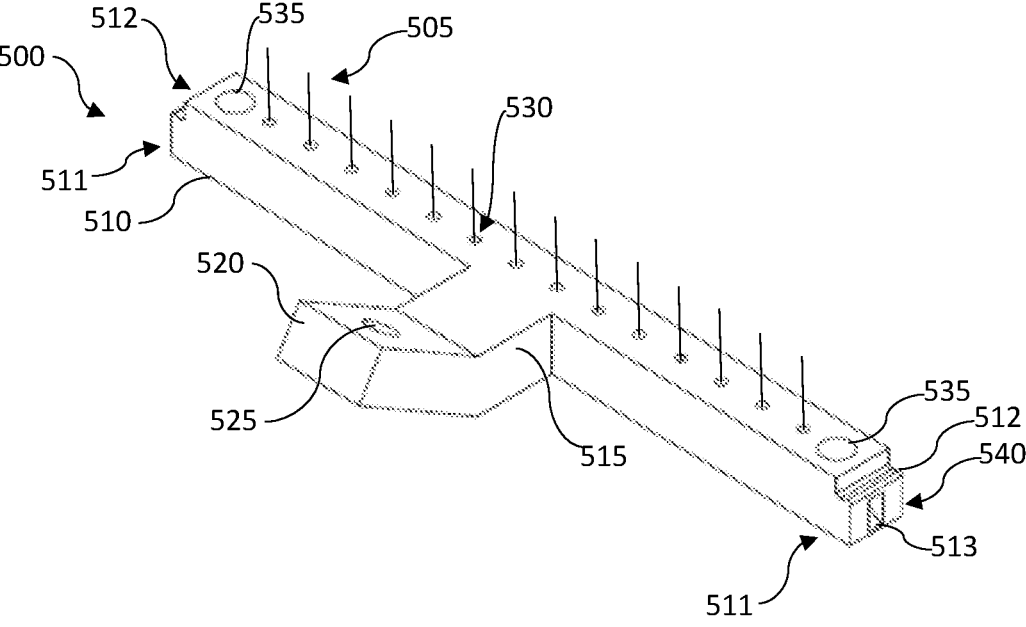
FIG. 5B depicts an upper bracket of a surgical training system, in accordance with the disclosed embodiments.

FIG. 5B illustrates aspects of the upper bracket 500. The upper bracket 500 can comprise a bracket body 510 with an orthogonal mounting brace 515. The mounting brace 515 can connect to the bracket body 510 at the nominal center of the bracket body 510. The mounting brace 515 is connected to an angled lever 520. The lever 520 include a mounting hole 525 configured to accept a connection assembly (e.g., a bolt and screw) associated with joint 415.

The bracket body 510 also includes a plurality of rivet mounting holes 530. The rivet mounting holes are configured to accept rivets 505 such that the base of the rivets are mounted in the rivet mounting holes, but the upper end of the rivets are exposed. It should be appreciated that the number of rivet mounting holes 530 and rivets 505 can be selected according to design considerations. Likewise in certain embodiments, the rivets 505 can comprise spikes, nails, poles, staples, or other such rivet like structures.

The distal ends 511 of the bracket body 510 include guidepost holes 535 configured to accept guideposts 555 when the lower bracket 550 and the upper bracket 500 are joined. The distal ends 511 further include stepped edge 512 configured to engage with a snap clip 560 on the lower bracket 550. A lock depression 513 is formed in the bracket body end face 540. The lock depression 513 is configured to accept a locking nub formed on the lower bracket 550.

Figure 5C:
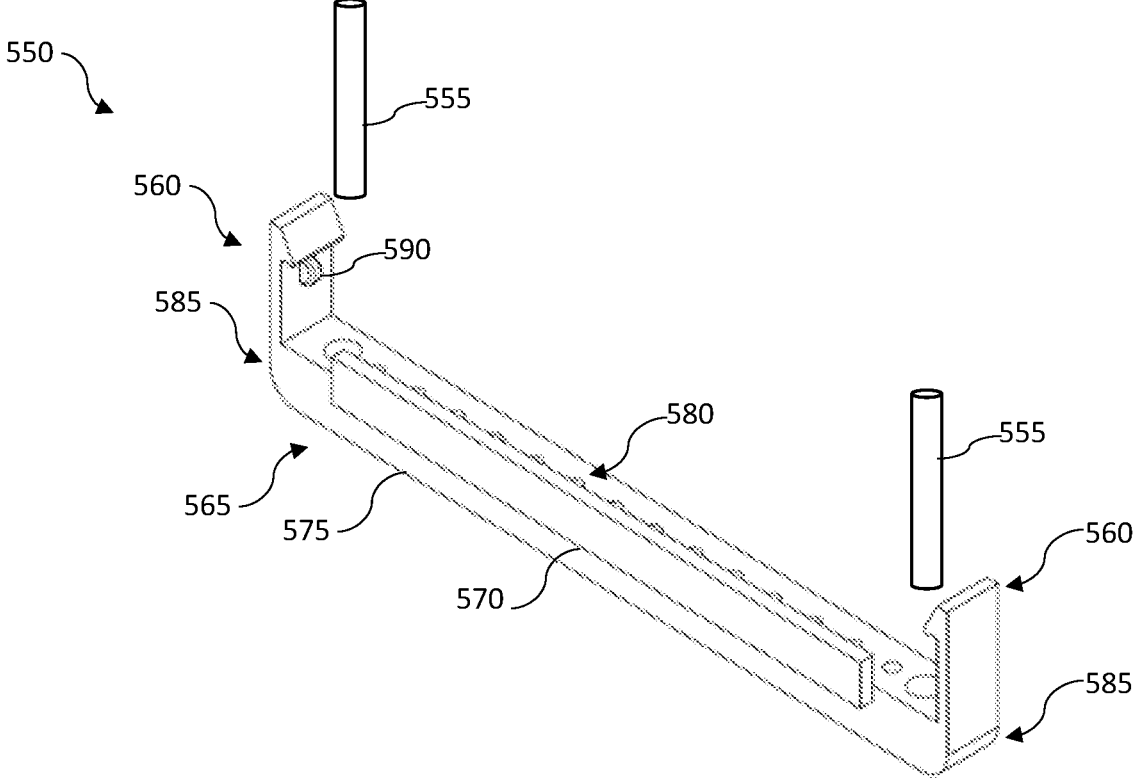
FIG. 5C depicts a lower bracket of a surgical training system, in accordance with the disclosed embodiments.

FIG. 5C illustrates aspects of the lower bracket 550 in accordance with the disclosed embodiments. The lower bracket 550 includes a lower bracket body 565. A rivet shield 570 can be configured along the outward facing side 575 of the lower bracket body 565. The lower bracket body further includes a series of terminal rivet guides 580. The terminal rivet guides 580 are landing positions for the rivets 505 as the lower bracket 550 and upper bracket 500 are joined.

Snap clips 560 are formed on the distal ends 585 of the bracket body 565. The snap clips 560 include a locking nub 590 configured to fixedly engage with the lock depression 513 on the upper bracket body, to securely engage the lower bracket 550 with the upper bracket 500.

The lower bracket body 565 finally includes lower guidepost mounting holes 595, into which the guideposts 555 can be mounted. The guideposts 555 ensure the alignment of the upper bracket 500 and lower bracket 550 as they are engaged to form the clamp 405 around the biomaterial 420.

In other embodiments other clamping configurations can be used. For example, in an actuated system the clamps can be installed automatically with no manual input of forces. The clamps can be held together by other means such as buckles rather than through a compliant mechanism. In other embodiments, magnets, including permanent magnets or electromagnets disposed in the upper bracket 500 and lower bracket 550 can be used to bias the brackets toward one another. In other embodiments, the biomaterial can include integrated parts that allow it to be fastened to the clamps or actuators. In certain embodiments, a guide system of holes molded in the proper locations in the suture material can be used as anchor points for fasteners.

Figure 6A:
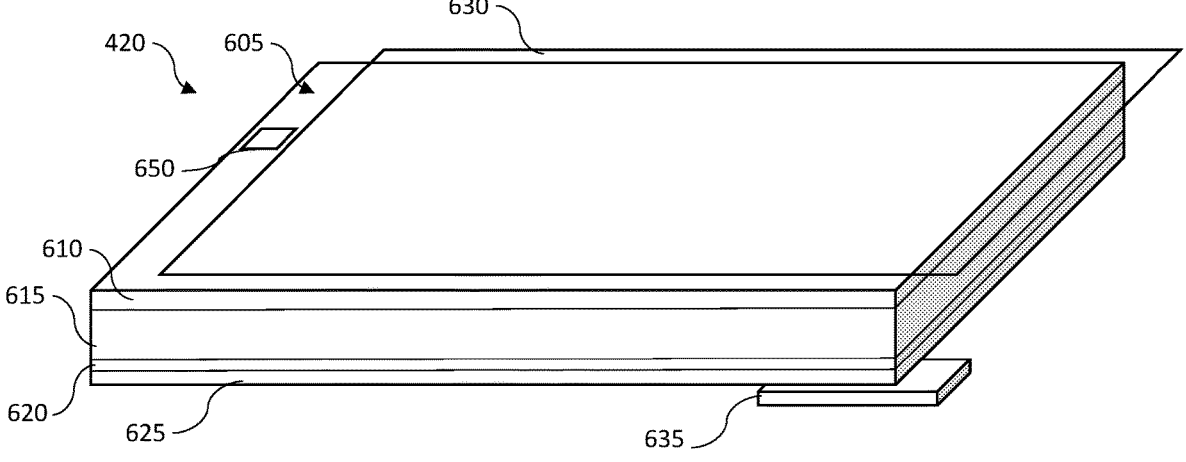
FIG. 6A depicts a biomaterial for a surgical training system, in accordance with the disclosed embodiments.

FIG. 6A illustrates aspects of the synthetic biomaterial 420 in accordance with the disclosed embodiments. The synthetic biomaterial 420 can comprise a material sheet 605 comprising one or more layers of material. The layers can include, but are not limited to, skin layer 610, fat layer 615, fascia layer 620, and muscle layer 625. The layers can comprise polymer/silicone blends with meshing to create synthetic tissue. In other embodiments, other materials can also be used.

In certain embodiments, the thickness of the layers can be adjusted to add realism to the training. For example, the thickness of certain layers can be adjusted to match a user selected Body Mass Index (BMI), which allows the user to practice with synthetic biomaterial simulating a person with a high BMI (thicker layers) or a low BMI (thinner layers). In certain embodiments, strain sensors 650 can be directly formed into the biomaterial and/or load cells 635 can be provided to measure the actuation force to provide quantitative feedback to the user.

Figure 6B:
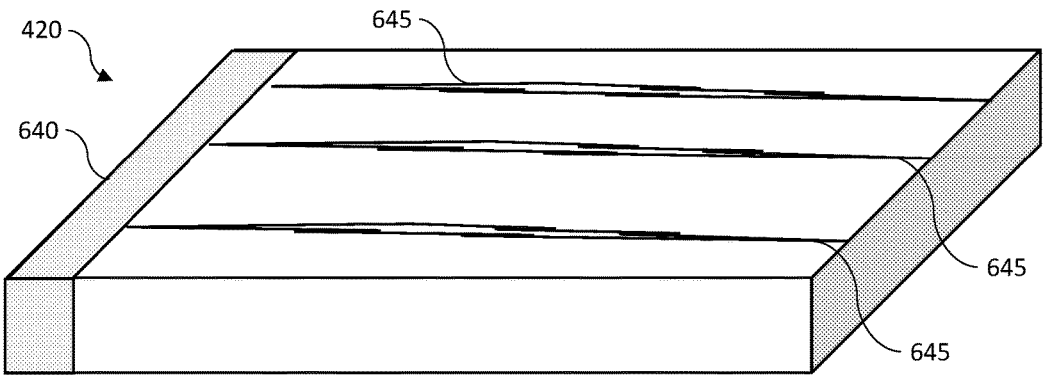
FIG. 6B depicts another embodiment of a biomaterial for a surgical training system, in accordance with the disclosed embodiments.

FIG. 6B illustrates further aspects of the embodiments. In certain embodiments, sections of biomaterial 420 can be configured to include a binding layer 640 on the edges, to more efficiently pair with the clamps. This may be of particular value where frequent replacement of the biomaterial is required. A reinforcing material can be used such as glue or a metallic-woven matrix material, such as aluminum mesh, on the edges of the biomaterial sections to easily integrate with the clamping system. A variety of alternative binding layers can also be used, including but not limited to pre-installed magnets which bind with magnets on the clamping system; hook and loop fasteners; fasteners; mechanical clamps such as tongue-and-clip connectors; teeth-pull strap mechanisms; and a snug fit style fittings where a peg fit snuggly in a hole, which uses tight dimensions to 'squeeze and hold'.

Figure 6C:
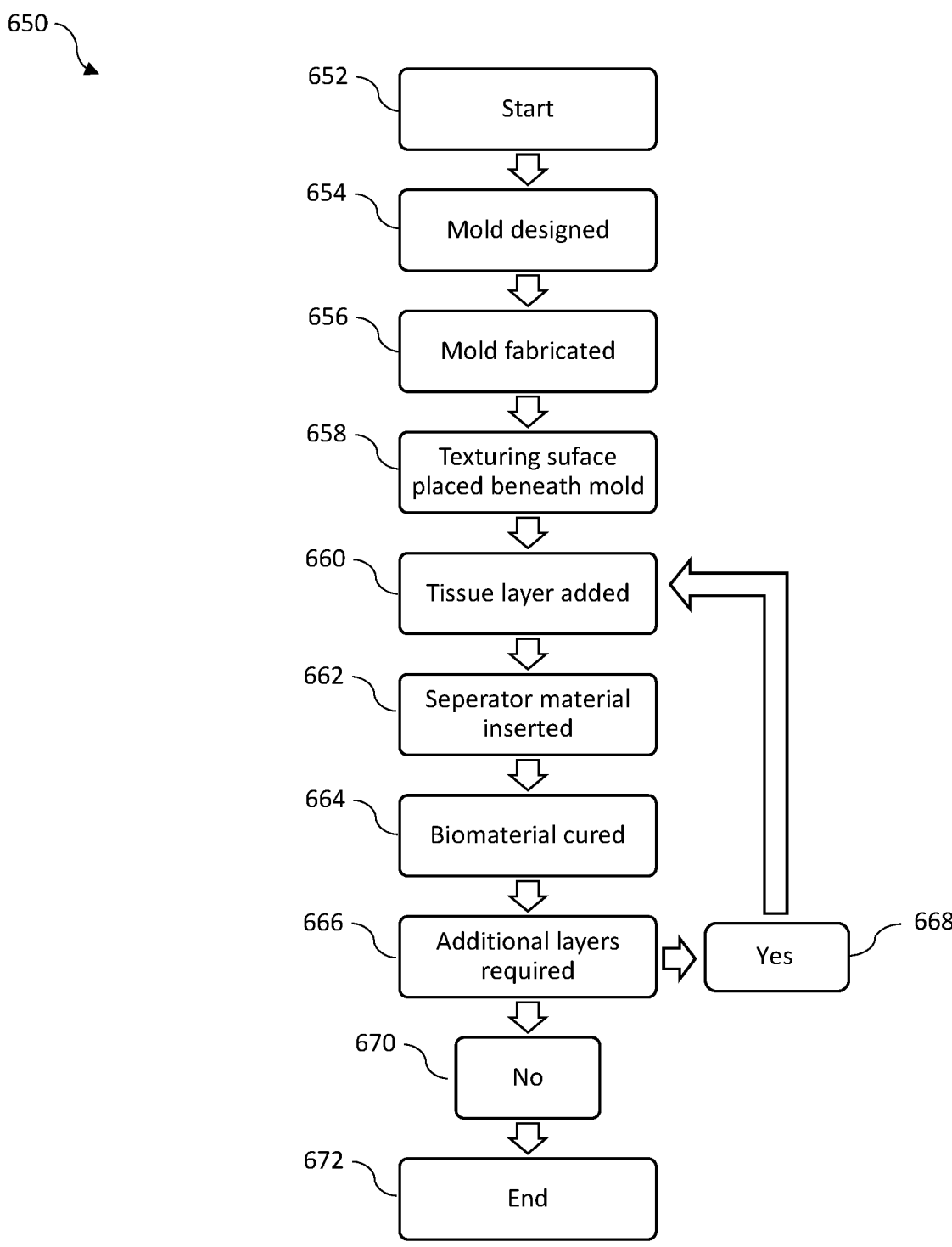
FIG. 6C depicts a method for manufacturing a biomaterial, in accordance with the disclosed embodiments.

In an exemplary embodiment, biomaterial 420 pads are fabricated with a multi-step molding method 650 illustrated in FIG. 6C, that allows for creation of diverse pads with different shapes, mechanics of tissue layers, and patient-specific features. It should be understood that the order of steps in method 600 is exemplary, and in other embodiments, other ordering can be used with departing from the scope herein. The method begins at 605.

Figure 6D:
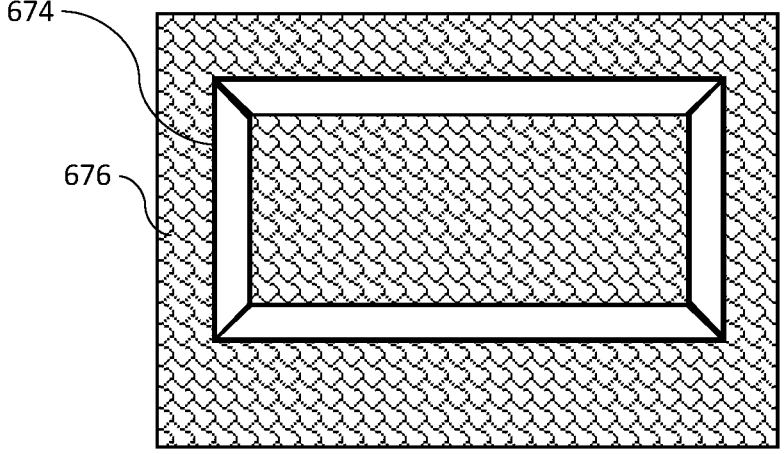
FIG. 6D depicts a mold for fabricating a biomaterial, in accordance with the disclosed embodiments.
Figure 6E:
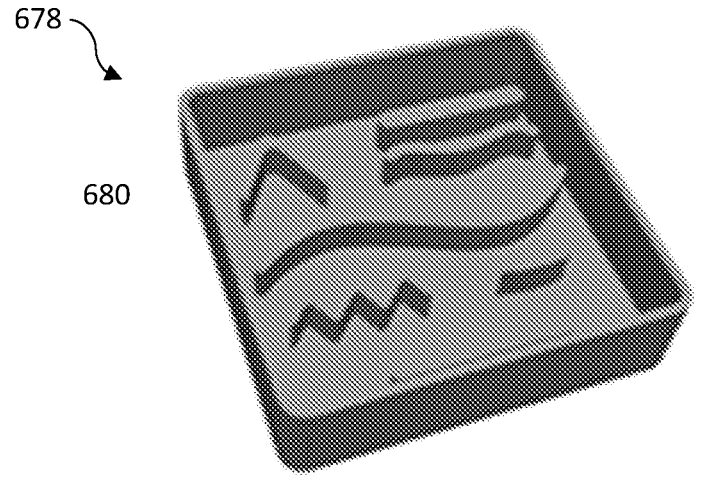
FIG. 6E depicts another embodiment of a mold for fabricating a biomaterial, in accordance with the disclosed embodiments.
Figure 6F:
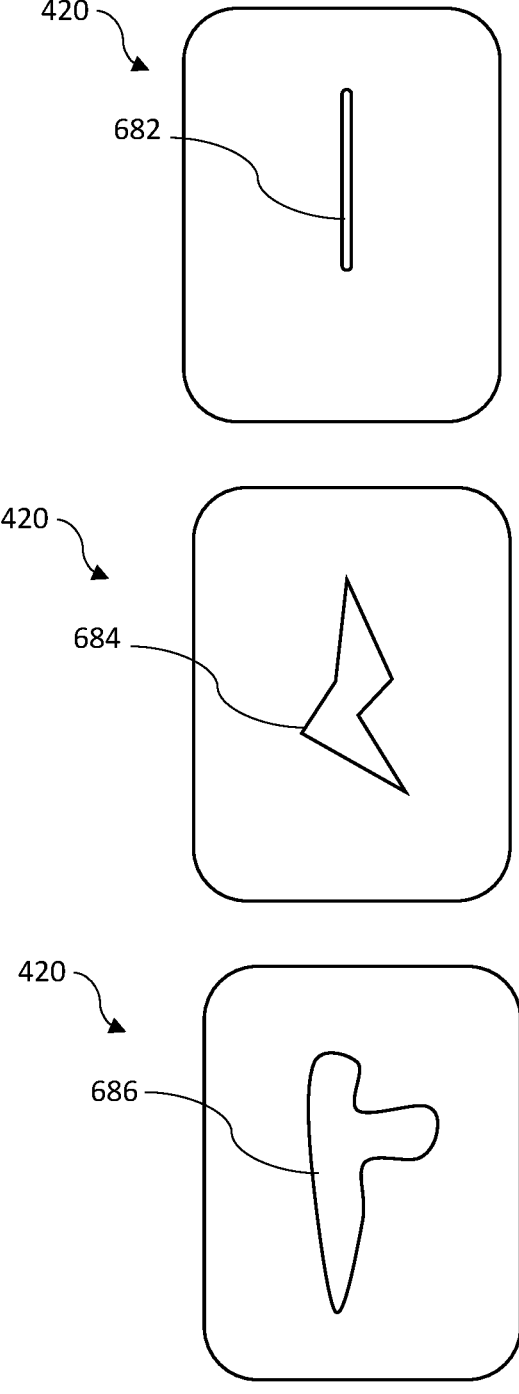
FIG. 6F depicts a biomaterial with a preformed wound, in accordance with the disclosed embodiments.

At step 654 the mold can be designed. This can include selecting the shape, surface area, and depth of the biomaterial 420 pad, as well as the selection of preformed wounds for suturing if desired. Next at step 656, the mold can be fabricated. In certain embodiments, the mold can be printed using a 3D printing system. In other embodiments, the mold can be configured using other such methods. FIG. 6D illustrates an exemplary mold 674 for a rectangular shaped pad. A texturing surface 676 can be placed below the mold, or can be inserted on the bottom of the mold at step 658. The texturing surface can comprise any material, such as a vinyl sheet, that mimics skin texture. FIG. 6E further illustrates an exemplary mold 678, with preformed wounds 680. FIG. 6F illustrates exemplary biomaterial pads 420 with a preformed straight wound 682, jagged wound 684, and protruding wound 686.

Figure 6G:
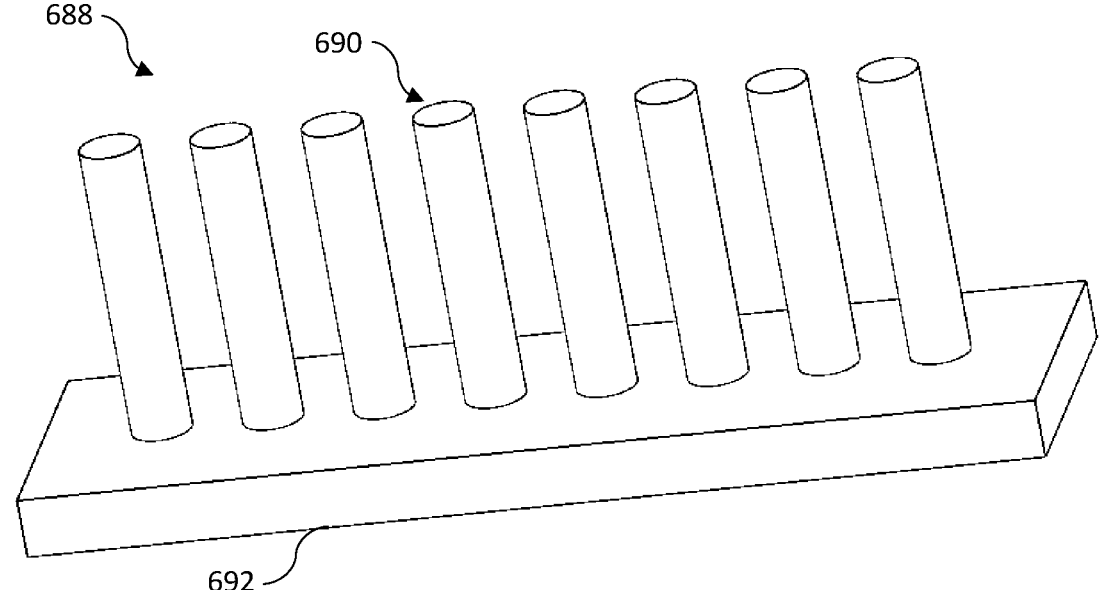
FIG. 6G depicts an insert for a biomaterial, in accordance with the disclosed embodiments.

In certain embodiments, structural elements can be embedded in the biomaterial 420 during the manufacturing process. FIG. 6G illustrates an insert 688 which can be integrated in a biomaterial pad that enable easy attachment to clamps. In the embodiment, a peg system 690 is formed on base 692. The insert can be disposed in the mold as layers are added. The insert 688 enables attachment to specified points on the device so the suture pad can be tensioned.

Once the mold has been designed and formed, the first tissue layer can be added as illustrated at step 660. At step 662 a separator material can be inserted over the tissue layer. The separator material can comprise powermesh fabric or other such material silicone to increase resistance to tear during suturing. It should be understood that each layer can be specially configured to replicate the type of tissue in that layer. For example, fat tissue layers can be configured with silicone and the addition of various fillers, foams, or powders that alter visual appearance and mechanics to create a more realistic tissue. This could include paper infill, foam bubbles, or a powdered finish, mixed into the silicone. It should be appreciated that the separator material is optional, and the addition of the separator material at step 662 is not always required. At step 664 the biomaterial layer can be cured.

At step 666 it can be determined if additional tissue layers are required. If additional layers are required at 668, the process can return to step 660 where an additional tissue layer is added. If all the necessary tissue layers have all been added at step 670, the material is now ready for use and the method ends at 672.

Figure 7A:
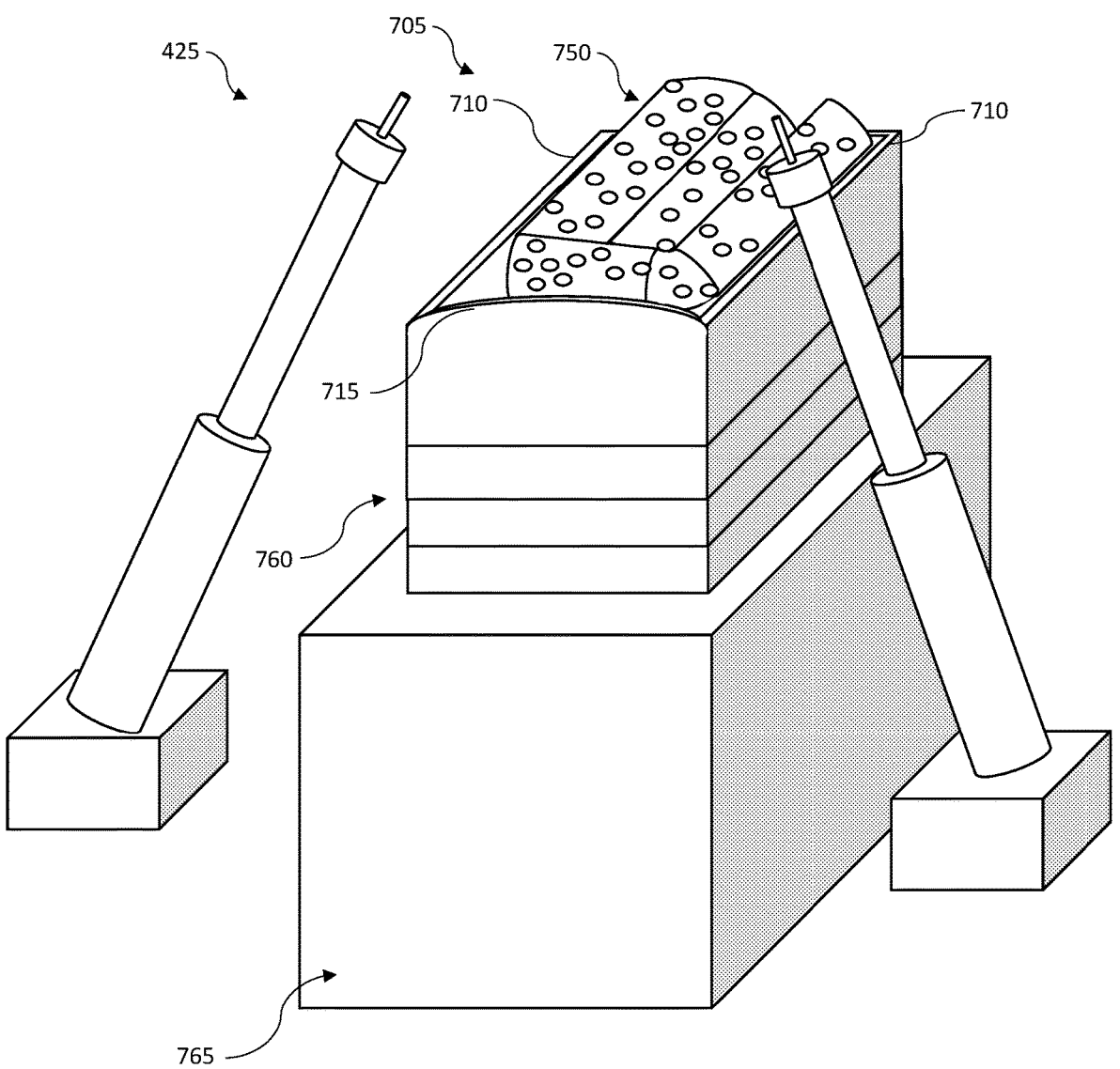
FIG. 7A depicts a surgical training system with synthetic anatomical features, in accordance with the disclosed embodiments.

FIG. 7A illustrates aspects of a patient body simulator 425 in accordance with the disclosed embodiments. The patient body simulator 425 can include a tray 705. The tray 705 can be manufactured via three dimensional printing, via molds, casting, or with other such manufacturing techniques. The long edges 710 of the tray 705 can be substantially flat and parallel to one another. The one or both of the short side edges 715 of the tray 705 can feature a convex curved profile extending above the respective long edges 710 of the tray 705. The convex curved provide of the short side edges 715 ensure that when the biomaterial 420 is stretched over the patient body simulator an appropriate upward force Fb is applied to the biomaterial.

The tray 705 is meant to hold synthetic anatomical features 750 of a human body. The synthetic anatomical features in FIG. 7A are exemplary, and are meant to simulate intestines 755. However, in other embodiments, other synthetic anatomical features such as organs, bones, connective tissue, fat, and bodily fluids, can be held in tray 705. A seal 630 can be applied over the tray 705 and synthetic anatomical features 750.

To that end, the disclosed systems can be configured to simulate suturing for different parts of the body, such as the head, arms or legs with appropriate biomaterials installed to represent the appropriate portion of the body. The physiology body portion of the tray can be replaced to represent the different curvature of parts of the body or geometries of a patient. Some further suturing scenarios can include hearing surgery and surface suturing of skin in addition to internal suturing. In certain embodiments, staples or glue can be used for closures.

Further organs can be integrated such as intestines with variable viscosity/density to represent different patient states, artificial lungs, artificial bones, skin defects such as moles or scars and variable amounts of moisture throughout the system. Internal actuators and control mechanisms can be introduced in the system for recreating patient heartbeat and other physiological mechanisms. The embodiments are designed to be readily adapted to most surgical operations and especially those that require some form of opening and closing related to suturing processes.

It should be appreciated that, in order to add realism, the surround of the system can be configured to resemble a human or animal form. For example, in certain embodiments, a mannequin style form with a void in the anatomical location where the training will take place can be used. The patient body simulator can be inserted into the void so that the form resembles a full patient body. It can be further appreciated that system can be configured to simulate suturing for different parts of the body, such as the head, arms or legs with appropriate biomaterials installed to represent the appropriate portions of the body.

It should be appreciated that the uppermost artificial organ is the suture biomaterial that has layers. Those layers can also include veins and arteries. The veins and arteries can transport fluid and be used to emulate sections of the human body and be distributed throughout the rest of the device such as a torso section. Custom layers of biomaterials can be designed or altered substantially to represent other anatomy, such as the Linea Alba. The layers of biomaterial can be attached together using fasteners, hook and loop, magnets, glue, and snug fit. Layers and biomaterial sections can be customized to represent a variety of body-mass indexes (BMIs). Biomaterials can have various colors, textures, and material properties to distinguish layers that are difficult to distinguish and better represent the colors in the body, and/or to indicate color-coded steps of a training procedure. Each layer can have different textures and can peel to better recreate the textures and separation of layers in the surgical operations.

The biomaterials can have heating elements 645 located internally or externally allowing the biomaterials 420 to have a realistic temperature. The biomaterials can be heated through the use of electrical resistors or by running warm fluid through tubes internally or externally of the biomaterials.

Figure 7B:
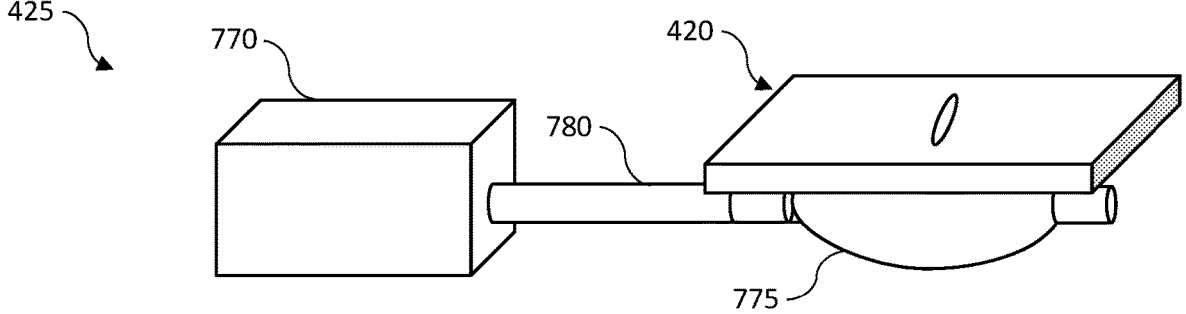
FIG. 7B depicts a synthetic breathing system, in accordance with the disclosed embodiments.
Figure 7C:
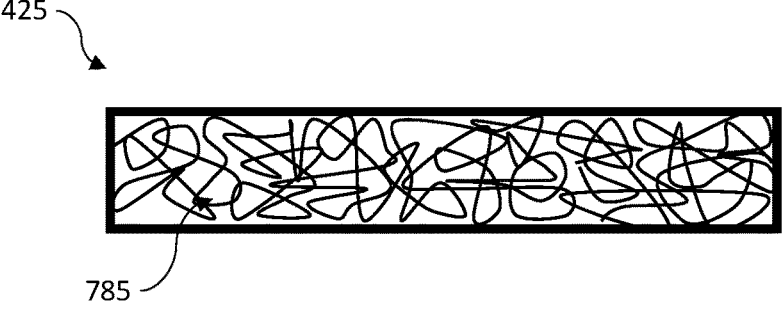
FIG. 7C depicts a cross sectional view of biomaterial, in accordance with the disclosed embodiments.

Fluid sacks 785 illustrated in FIG. 7C, within the biomaterial layers allows fluid to be stored inside the biomaterials. When the biomaterials are cut, the individual fluid sacks will be cut as well allowing the fluid to be released to simulate bleeding.

FIG. 7A further illustrates aspects of the patient body simulator 425 in accordance with the disclosed embodiments. The patient body simulator 425 can include stackable height adjustment blocks 760. In addition, various additional body simulation devices can be provided in cabinet 765. Additional body simulation devices can include circulatory simulators to drive blood, simulate pulse and blood pressure, respiratory simulators to simulate lung function and respiratory cycles, and other such bodily functions. The body simulation device can include a computer system as illustrated in FIGS. 1-3 which can simulate patient conditions including health metrics, patient conditions, acute patient conditions, etc. The patient simulation device 425 can thus be used to provide additional realism to the training.

FIG. 7B illustrates an exemplary embodiment of an aspect of the patient simulation device 425. In this embodiment, a ventilation pump 770 connected to a synthetic lung balloon 775 with tubing 780. The pump 770 can inflate and deflate the synthetic lung balloon 775 to mimic the motion associated with real inhalation and exhalation. Higher sudden pressure can be sent through the device to simulate a cough or other abnormal breathing patterns.

The breathing mechanism allows for regular pressure to be applied and released to the biomaterial. In certain embodiments, pump 770 can comprise a cyclical air pump that pumps air to the bag 775 that inflates/deflates under the biomaterial. The air can be released by pressure, or a mechanical mechanism can push air from the bag 775 to deflate it. The source of the air can comprise a cyclical pump that turns on and off, a rack and pinion cyclical system, or a continuous stream of air that is diverted appropriately with valves.

Figure 8:
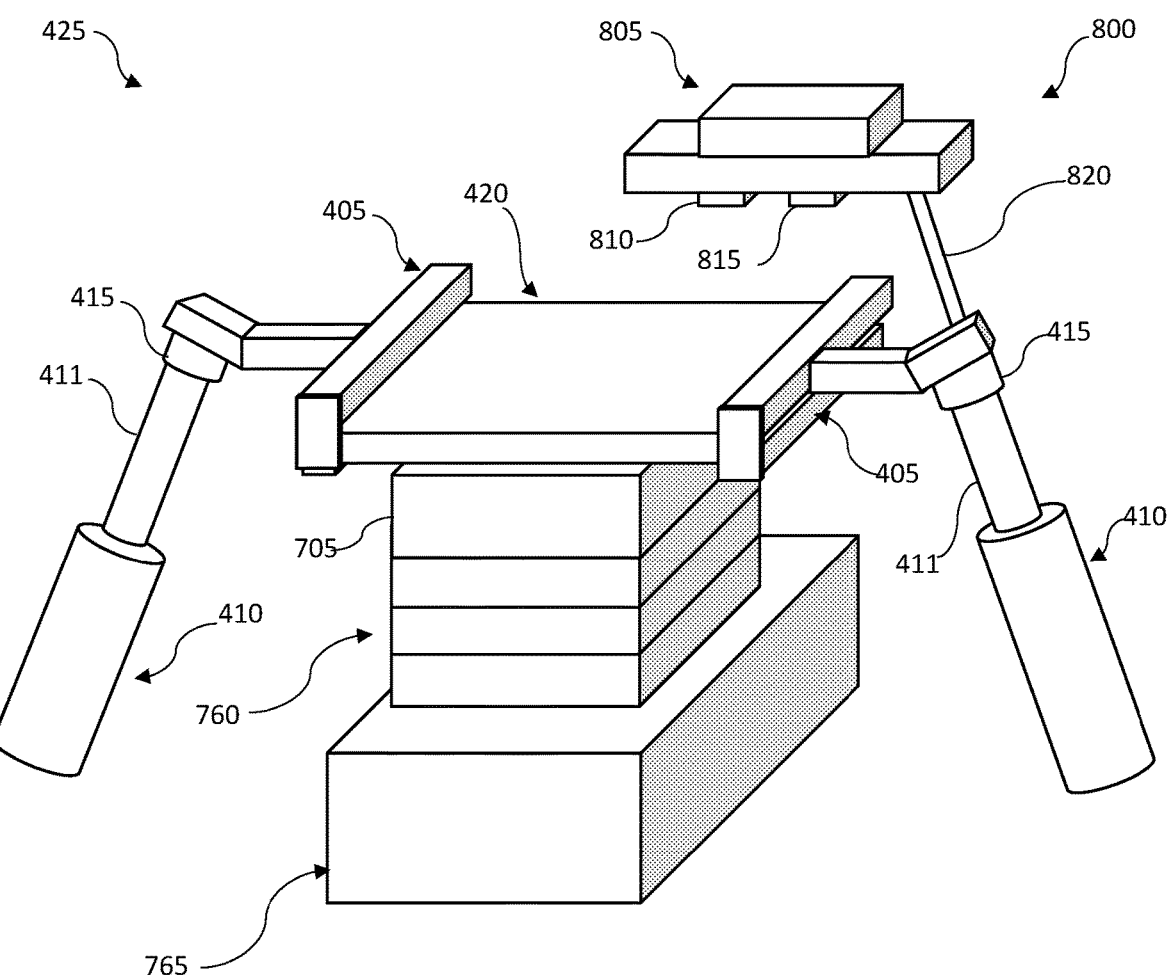
FIG. 8 depicts a camera system as a part of the surgical training system, in accordance with the disclosed embodiments.

FIG. 8 illustrates an additional embodiment of a surgical training system 800 in accordance with the disclosed embodiments. In this embodiment, the system 800 includes the surgical training system 400 along with a training assistant 805. The training assistant 805 can be embodied as an computer system including but not limited to a smart phone, tablet device, or computer with peripheral devices. In FIG. 8 the training assistant 805 is illustrated as a computer system operating with an overhead camera 810 and projection device 815 mounted with an adjustable mounting pole 820. The projection device can include but is not limited to a projector, laser, or light source, or other such projector.

The training assistant can be preferably connected to a computer system as illustrated in FIGS. 1-3 via wired or wireless connection. In an embodiment, the training assistant 805 can be configured to collect images of the biomaterial 420 as the trainee performs procedures. In more additional embodiments, the training assistant 805 can be configured to collect real time audio and video of procedures being performed by the trainee and can provide real time audio feedback, or visual feedback via the projection device 815.

Figure 9:
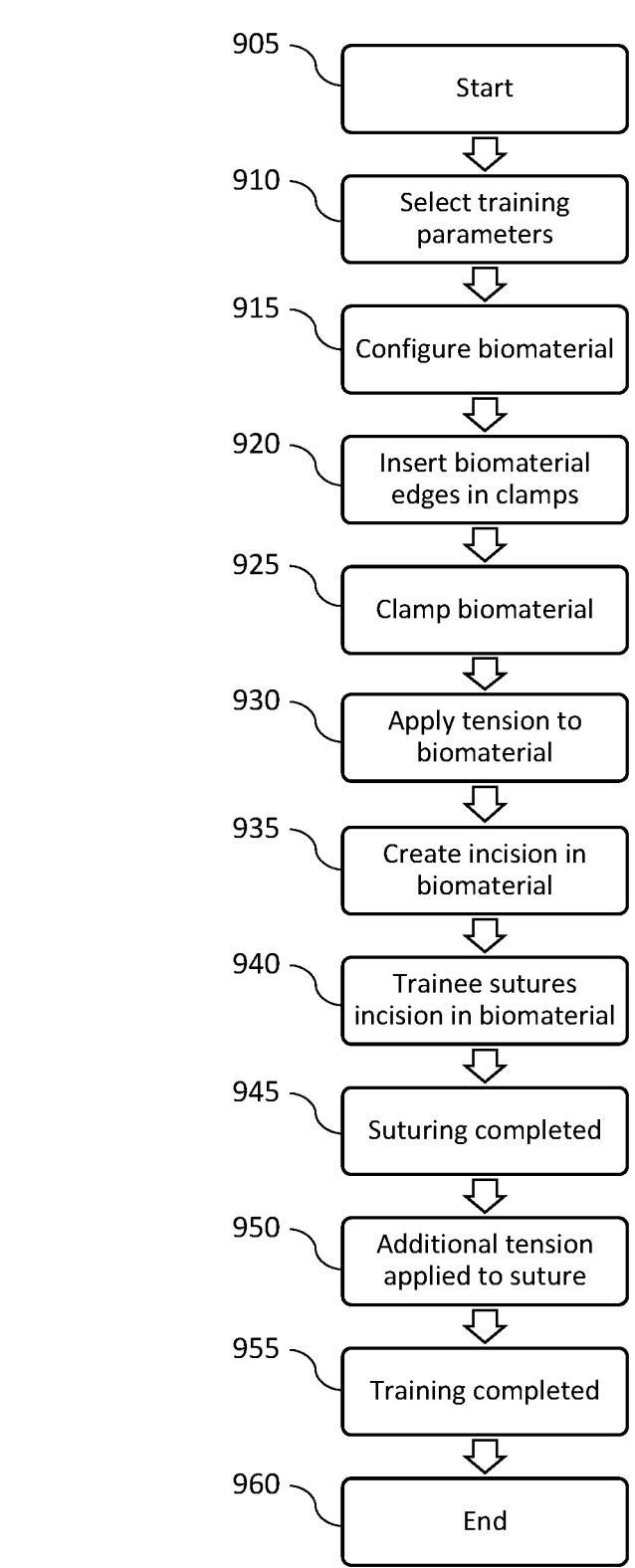
FIG. 9 depicts a method for surgical training with the disclosed systems, in accordance with the disclosed embodiments.

FIG. 9 illustrates steps associated with a method for surgical training 900 in accordance with the disclosed embodiments. It should be appreciated that this method can be implemented with any of the disclosed embodiments and reference to certain systems is meant to be exemplary. The method starts at 905. At step 910 parameters associated with the training can be selected. In certain embodiments, this can include selecting the surgical training procedure, such as a laparotomy, BMI associated with the biomaterial, physical conditions of the simulated patient, etc. The associated biomaterial and synthetic anatomical features can be selected at step 915.

Next, an edge of the biomaterial can be inserted into the clamp at step 920, and clamped as disclosed. The body simulator can be inserted beneath the biomaterial, and the opposing side of the biomaterial can be clamped by the second clamp at step 925. With the biomaterial secured between the two clamps and over the body simulator, the actuator can be used to apply tension to the lever on one or both of the clamps as shown at step 930. The angle of the levers and the shape of the tray ensure the tension accurately reflects a real human body.

The system is now ready for a trainee to begin practicing a medical procedure as shown at step 935. In certain embodiments, this can include making an incision in the biomaterial. The trainee can further practice additional surgical techniques. When those techniques are complete, the trainee can suture the biomaterial together as shown at 940. The layers of the biomaterial are configured to simulate real human anatomy so the suturing can proceed through one or more layers. The completed suturing at step 945, can be followed by the additional application of tension at step 950 so that the trainee can see the results of the suturing under tension. At this point, at step 955, additional training or guidance can be provided to the trainee, this can include insights on the statures, procedures completed etc. at which point the method ends at 960.

Figure 10:
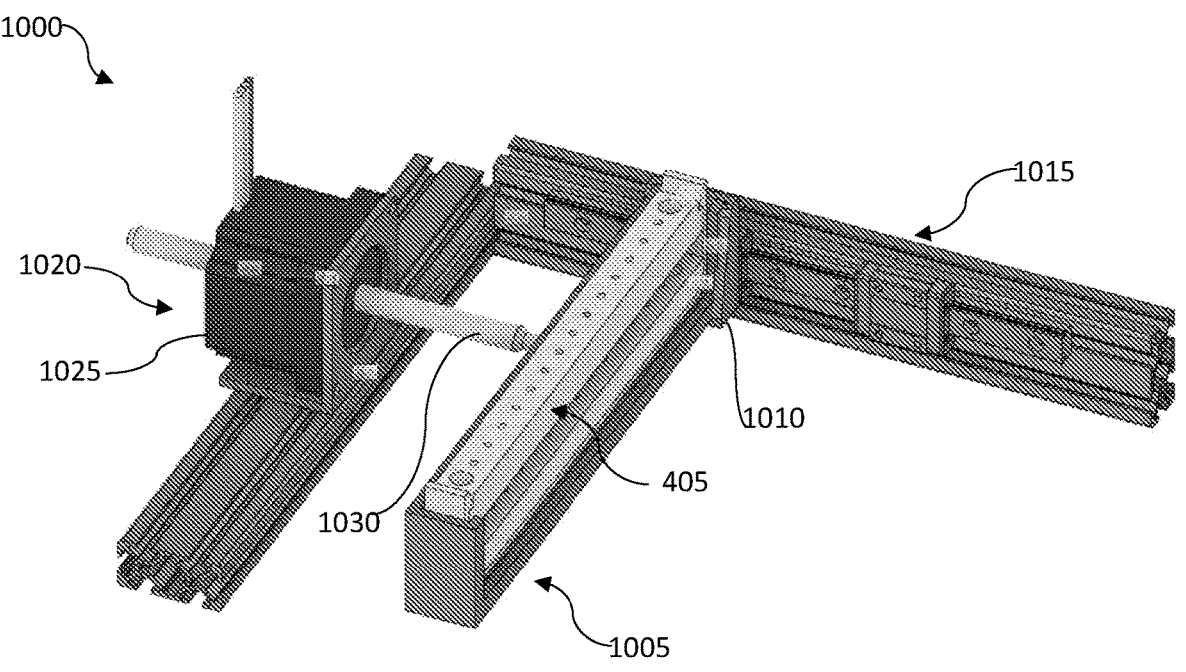
FIG. 10 depicts a stepper motor for use with a surgical training system, in accordance with the disclosed embodiments.

In certain embodiments, a system can comprise an actuated system as illustrated in FIG. 10. In certain embodiments, a motor-drive screw system 1000 can be used as the primary actuation mechanism. As in the other embodiments, the motor-drive screw system 1000 includes clamps 405 mounted to a clamp holder 1005, with clamp holder brackets 1010. A set of guide rails 1015 engages the clamp holder bracket 1010 and allows the clamp to slide. A motor 1020 mounted in a motor mount 1025 can drive a screw 1030, which is in contact with the clamp holder backet 1010.

The motor-screw drive system 1000 works with the biomaterials loaded into the clamps. When the motor is turned on, it drives the lead screw 1030 which can freely move in and out of the motor 1020. In doing so, the lead screw 1030 will drive the clamp holder, as programmed, to glide along the guide rails 1015. The tension of the biomaterial can be adjusted. This allows precise tuning of mechanical strain in the biomaterial.

Figure 11:
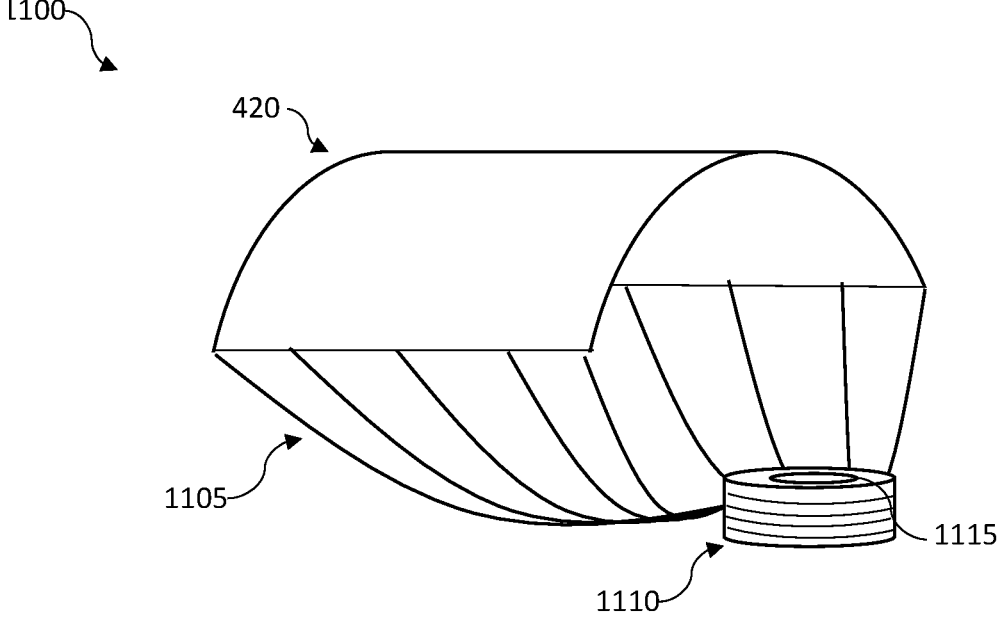
FIG. 11 depicts an alternative tensioning mechanism, in accordance with the disclosed embodiments.

Various alternative tensioning mechanisms can be used in accordance with the disclosed embodiments. For example, FIG. 11 illustrates a spool and cable system 1100. The spool and cable system 1100 can comprise a series of cables 1105 operably connected to a mechanical spool 1110 used to adjust the tension in the cables 1105 simultaneously. The cables 1105 can be operably connected to, or integrated throughout, the biomaterial 420 section, with the spool 1110 located beneath the working area. The cables can be spooled onto the spool 1110 by turning the spool, which provides omnidirectional pulling when the spool 1110 is tightened. The spool 1110 can also be released with release button 1115 to return the cables 1105 to their original tension. As shown, the spool 1110 can be controlled electronically by a user-input controlled motor, or controlled manually. This embodiment can be automated, in which case it is possible for this system to assist in tension adjustments in other embodiments. When pulled uniformly, uniform tension in the biomaterial can be achieved. It is also possible to attach the clamping mechanism on adjacent sides of the biomaterials, not just the two opposite sides as depicted in FIG. 11.

Figure 12:
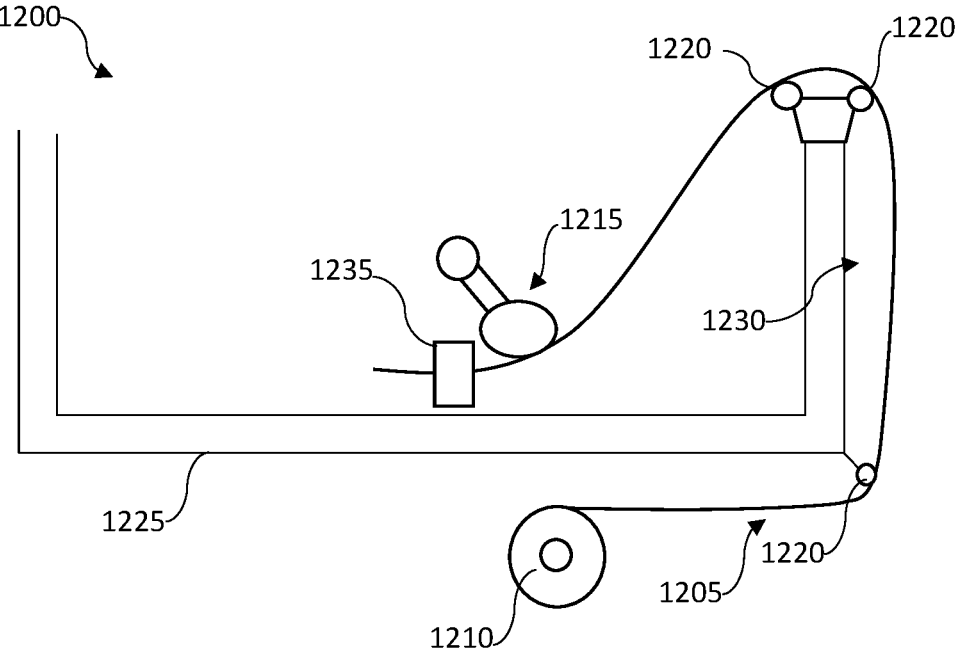
FIG. 12 depicts a roll dispensing system for biomaterial, in accordance with the disclosed embodiments.

In another embodiment illustrated in FIG. 12, an auto feeding system 1200 for conveniently cycling sheet biomaterial 1205 is disclosed. It should be appreciated that the sheet of biomaterial can include any of the aspects of the biomaterial 420 disclosed herein. The auto-feed system 1200 allows a spooled sheet of biomaterial 1205 to be fed into an operable position automatically. The biomaterial sheet 1205 can be spooled onto spool 1210. An auto-feed drive 1215 can pull the sheet of biomaterial along rollers 1220. The frame 1225 can define the operational section 1230. After a section of biomaterial sheet 1205 is used, the auto-feed drive can be used to pull the used biomaterial out of position and a new section of biomaterial into the operational section 1230. A cutter 1235 can be used to cut off used biomaterial sections for disposal.

Figure 13:
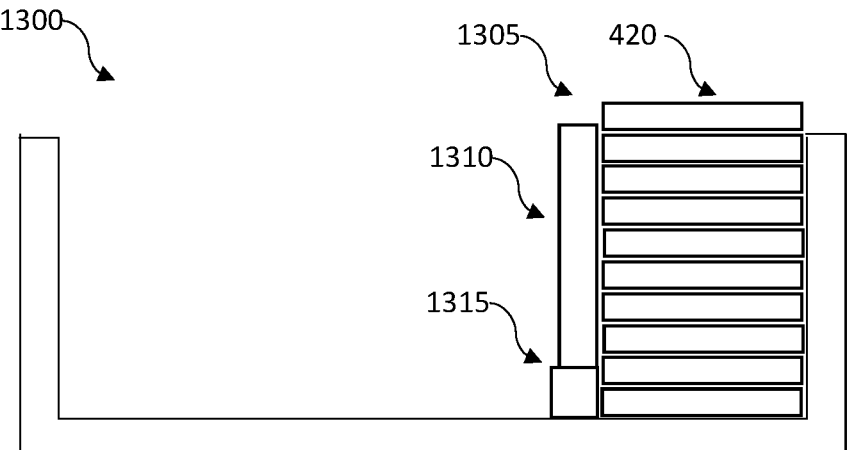
FIG. 13 depicts a biomaterial dispensing system, in accordance with the disclosed embodiments.

FIG. 13 illustrates an auto feeder system 1300. In this embodiment, a stack 1305 of biomaterials 420 can be precut and loaded into chute 1310. The chute 1310 can include a mechanical feeder 1315 that feeds the precut biomaterial to the top of the chute for use.

In certain embodiments, linear actuators can be positioned in different orientations to create the desired tension. One such orientation can include horizontally mounted actuators on the same plane as the biomaterial. This can be accomplished using either a single horizontally mounted linear actuator in a cantilevered system that is fixed on one end; two horizontally mounted linear actuators working in tandem against one another; or three or more horizontally mounted linear actuators for more precise control over applied forces. Another embodiment includes vertically mounted linear actuators using belts, pulleys, or rolling cylinders to translate the linear pulling motion from the vertically mounted linear actuator(s) into horizontal pulling force on the suture biomaterial. In other embodiments, the actuator can comprise manual tensioning devices, such as with a hand crank or screwing mechanism. In certain embodiments a pneumatic gripping system or spring loaded mechanism can be used to store and release power.

Figure 14:
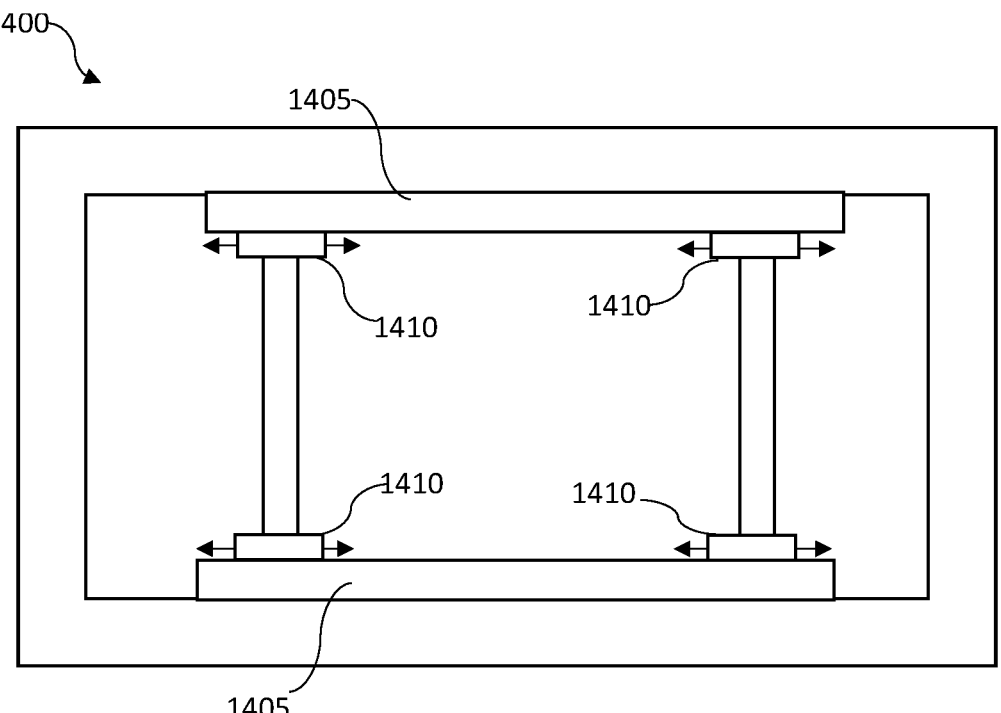
FIG. 14 depicts an alternative tensioning mechanism, in accordance with the disclosed embodiments.

In another embodiment, illustrated in FIG. 14 an actuated guide rail system 1400 can be used. The system 1400 comprises linear or curvilinear rails 1405 which can support a rolling block 1410 on wheels which runs along the guide rails 1405. The block 1410 movement is controlled by electric motors inside the body of the block 1410. Applications of this system 1400 include, but are not limited to, binding the suture biomaterials directly to the block with clamping mechanisms so that desired forces can be applied to the biomaterials without the need for linear actuators. Movement along the horizontal axis, down the guide rails 1405, by the block when fixed to the materials results in the application of a linear force to the material in said direction.

It should be appreciated that although the embodiments disclosed herein are generally designed to apply linear forces from two points on the same plane, in alternative embodiments alternative directions in which linear force is applied are possible. This includes bi-directional force application, by mounting the force applicators (actuators, motor-screw drive, actuated guide rails, etc.) on the adjacent side of the suture biomaterials, or following curved rail pathways to apply tensions according to curvatures of human body.

Figure 15:
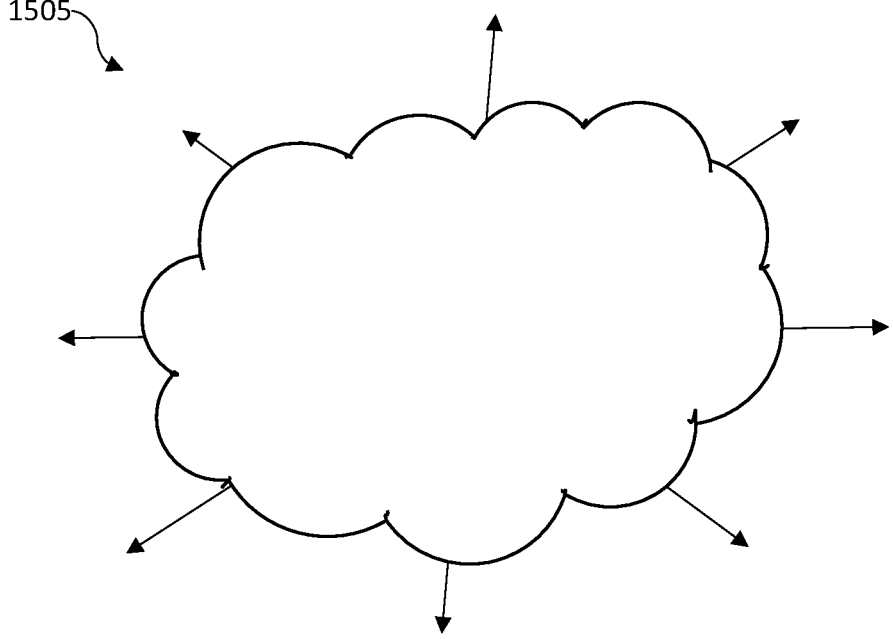
FIG. 15 depicts multidirectional tensioning of a biomaterial, in accordance with the disclosed embodiments.

In addition, omnidirectional pulling is also possible by mounting force applicators on all sides of the suture biomaterials and/or on the corners of the biomaterial. In certain embodiments forces in multiple directions can be applied simultaneously given the biomaterials are not limited to a rectangular shape. FIG. 15 illustrates an exemplary embodiment of a biomaterial 1505 with an oval or circular shape being pulled in multiple directions.

In other embodiments the clamps can be held together by other means such as buckles rather than through a compliant mechanism. In other embodiments, the system can be provided in varying sizes suitable for simpler testing, such as basic sutures for medical students that do not involve the complexity of the abdominal wall.

Figure 16A:
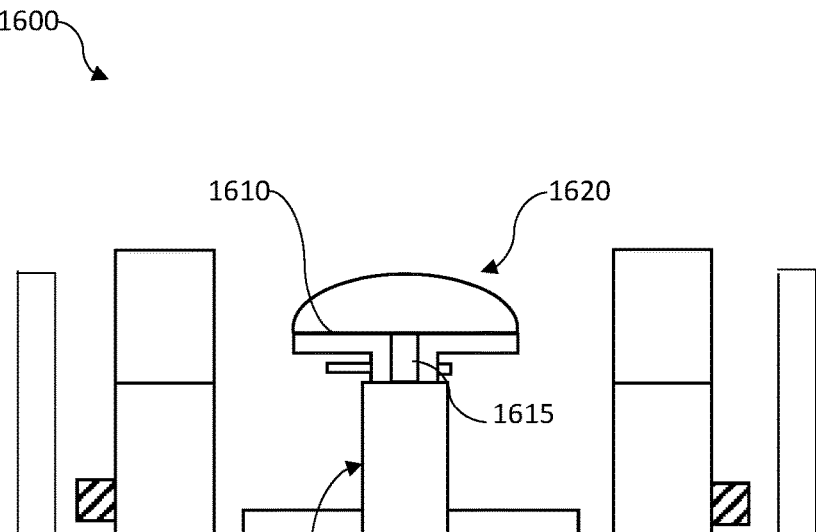
FIG. 16A depicts a biomaterial tensioning system, in accordance with the disclosed embodiments.

FIG. 16A illustrates an elevation view of a lower structure of the system which can be used to exert pressure on the biomaterial. One such arrangement comprises a riser system 1600 with a vertically mounted linear actuator(s) 1605, which can be fixed to a moving plate 1610 on the upper portion of the piston 1615. Upward movement by the single post actuator 1605, and attached moving plate 1610 applies a force over the area of the plate 1610 when pushed onto the suture biomaterials, resulting in a simulated pressure being applied. The piston can generate upward and downward force, in certain embodiments, to simulate inhalation and exhalation. Artificial organs may still be housed on or above the moving plate 1610. The actuator(s) system 1600 can be comprised solely of a combination of electric, hydraulic, or pneumatic powered actuator(s). This system can be adapted to integrate more than one actuator for more precise force application control.

Figure 16B:
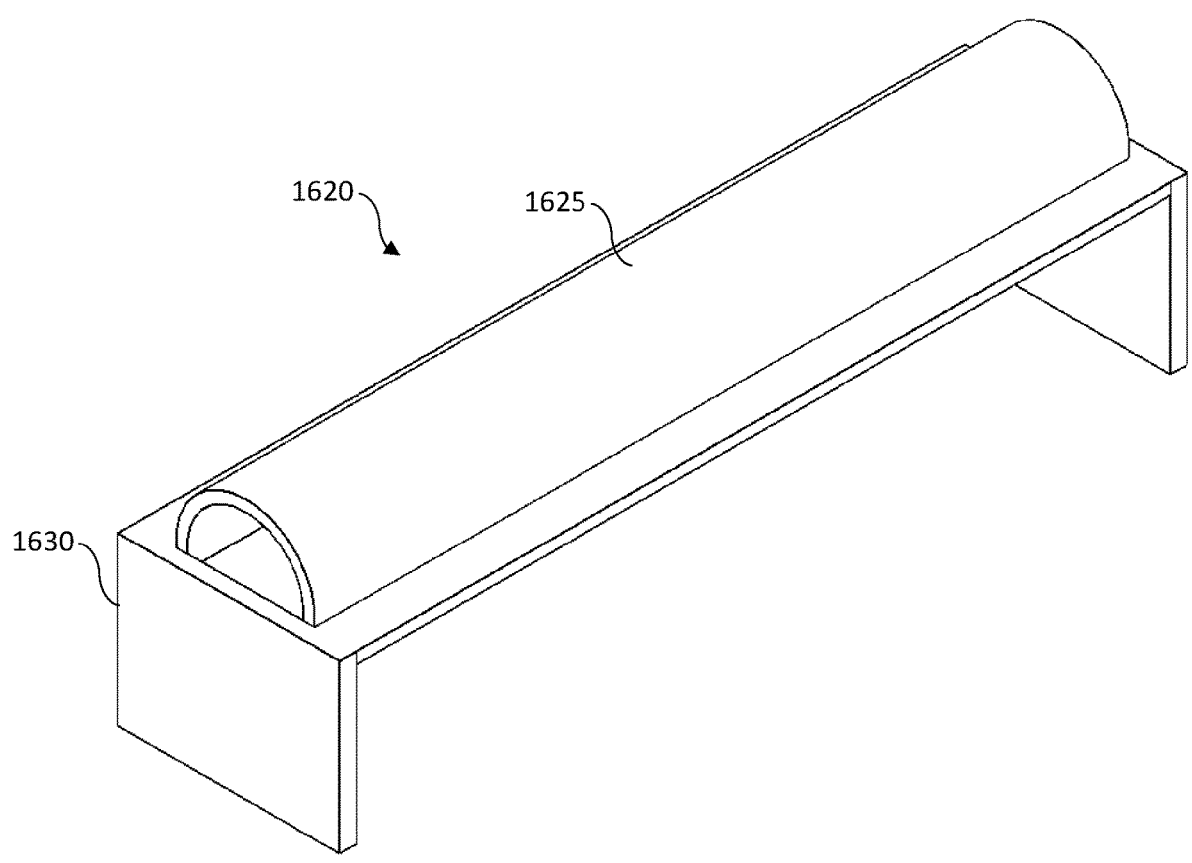
FIG. 16B depicts an attachment for mechanical force transfer, in accordance with the disclosed embodiments.

The plate can include an actuator attachment 1620 further detailed in FIG. 16B. The actuator attachment 1620 is configured with a half rounded upper surface 1625, formed on a stand 1630. The rounded surface distributes pressure equally and naturally on the suture biomaterial.

Figure 17:
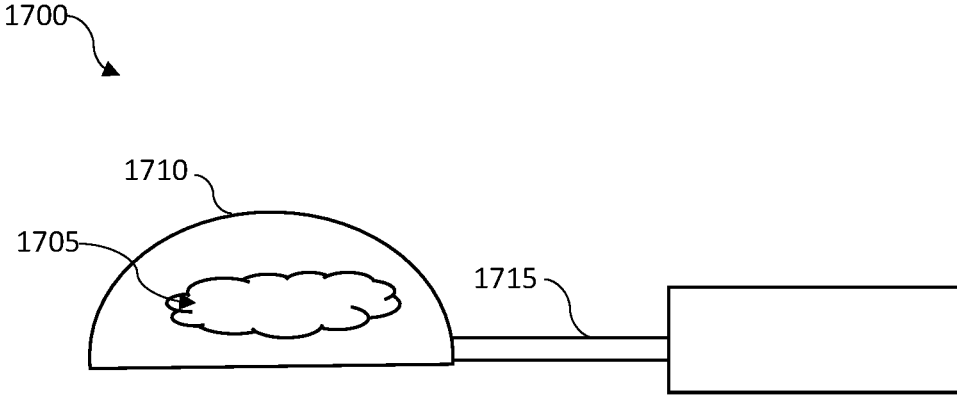
FIG. 17 depicts a pressure driven riser system, in accordance with the disclosed embodiments.

In additional embodiments a fluid-containing bladder and bag system 1700 as illustrated in FIG. 17, can provide the same simulation of pressure and patient breathing. One such implementation illustrated in FIG. 17, comprises compressed air 1705, or another fluid being injected into a flexible-walled pressure vessel 1710, for example a bag, resulting in an increase in overall volume. This increase in pressure through compressed air injection port 1715 expands the bag outward, to simulate intra-abdominal pressure. Similarly, oscillation can be controlled to simulate patient breathing.

Another mechanical solution utilizing principals similar to the bladder and bag system 1700 includes a bypass mechanism. A second pressure container in the form of a bag or bladder can be attached to the first by a switch-controlled gate. When the gate is open, volume can be reduced on one pressure container to increase the pressure on the other. Valves can be integrated to bleed pressure when necessary. Inflation and deflation of the primary bag can be controlled either manually by a hand squeeze-style pump or automated by electronic control from the user. Inflation can drive a simulation of intra-abdominal pressure, and looped inflation and deflation can represent patient breathing.

Figure 18:
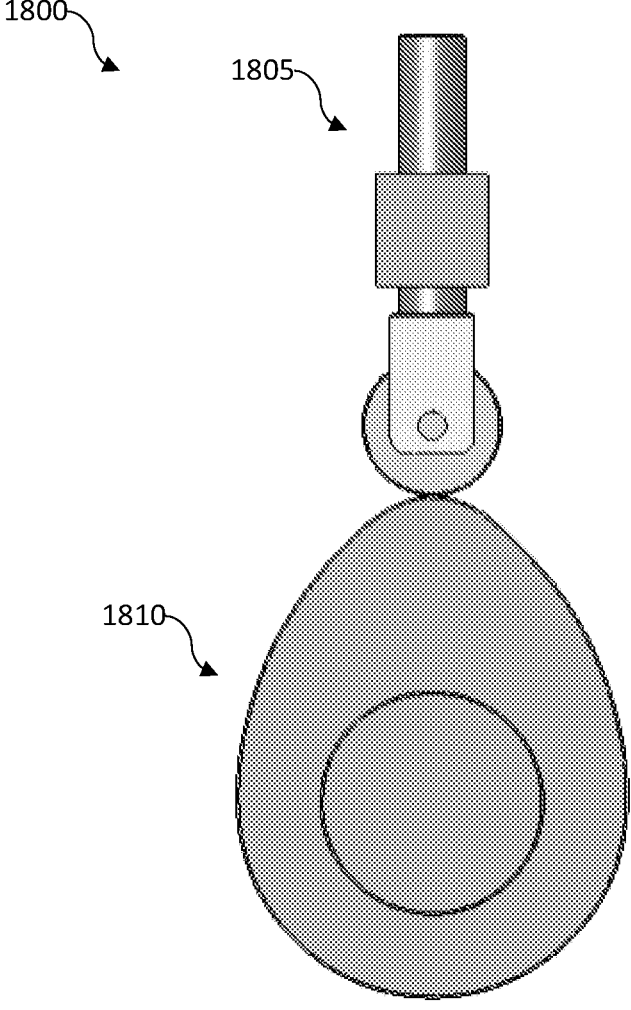
FIG. 18 depicts a cam driven system for mechanical tensioning, in accordance with the disclosed embodiments.

FIG. 18 illustrates mechanical alternatives to simulating intra-abdominal pressure and patient breathing include a cam and follower system 1800. The system 1800 oscillates an upper piston 1805 in a predictable pattern based on the shape of the cam 1810. Similarly, this can be used to simulate intra-abdominal pressure by attaching the upper piston 1805 to a flat or curved plate. Stopping the cam 1805 movement at a specific instance when the piston is extended to a desired length will apply an upward force through the upper piston 1805 when it is compressed against the upper parts of the system. This provides simulated pressure over a section of the suture biomaterials and the organ tray where applicable. Repeated, looping oscillation of the cam and follower system 1800 by the same means can be used to simulate patient breathing.

Figure 19:
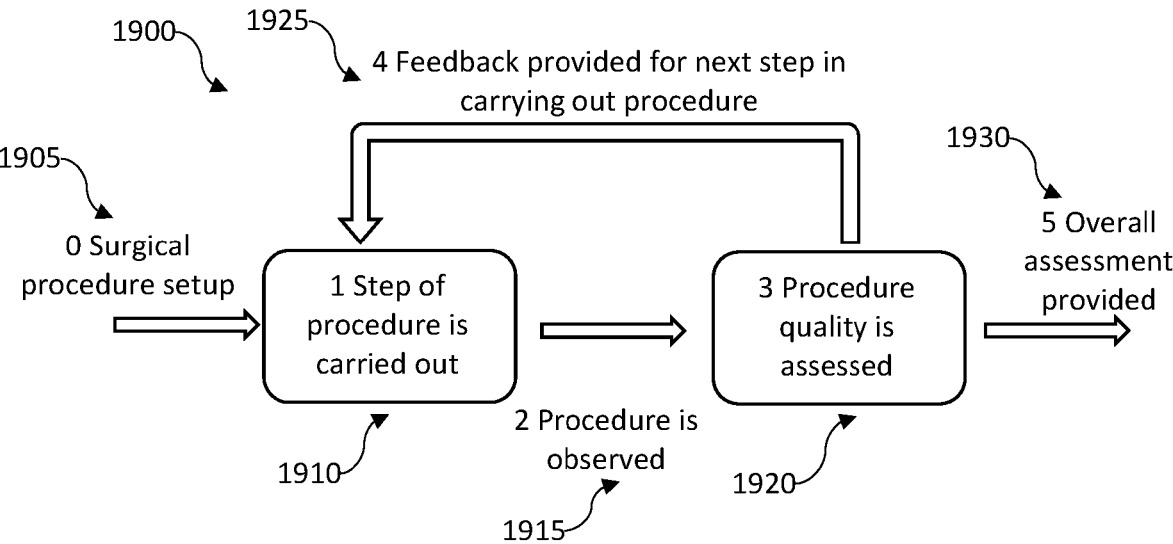
FIG. 19 depicts a surgical training method, in accordance with the disclosed embodiments.

FIG. 19 illustrates a method 1900 that can be conducted with a user, a user with instructor, a user with a computational guide, or a computational system providing assessment with an automated suture/surgical system. The basic method 1900 is a loop which begins at 1905 where the surgical procedure is setup. This procedure could be a laparotomy or other type of surgery, including but not limited to abdominal wall surgery, heart surgery, or skin closure for a skull.

Next at step 1910, the surgical procedure is carried out. This can include, for example, placing sutures or staples or opening the skin by a user. In other cases, this can be carried out by a human user or automated system or human operating a surgical assistant. Steps include opening, closing, and other surgical actions. Next at 1915 the procedure is observed either by a user, a camera, or other detection device.

At step 1920 the quality of the procedure step is observed either through user/instructor assessment, or machine learning, finite element analysis, or mechanical tension testing. For example, a light overlay can demonstrate the next point place for a suture/staple, a signal can be sent to a machine to direct it to the next location, there can be an expert surgeon recommending where to place the next suture. In certain embodiments, aspects can include an augmented reality overlay, a laser guided system, and/or virtual reality. Feedback can also be sensory feedback to modify the difficulty of the procedure such as adding coughing or changing heartrate.

Feedback can be provided at 1925 to the user in terms of what they are suggested to do next or to demonstrate the forces/achieved success of the surgery which then leads to additional loops of steps 1905-1925, until the surgery is completed. Finally at step 1930 an overall assessment is provided for surgery success that can be objective or in relation to other users. After full completion there is an assessment provided for the final end procedure and assessment of process throughout the entire surgical procedure. This can include tensioned mechanical analysis to determine feedback, which can even be destructive at end so there is a numerical output for its strength. The overall goal of the feedback loop is to help user with aid of the automated systems train to improve surgical technique with high quality feedback provided that enables a faster development of successful technique.

Feedback loops for learning can vary in length. For instance, the entire learning session could take place at once, during a lab session with a user/professor, or over a week if the user takes part of the system home to practice and a final assessment isn't given until the professor checks it at the end. Automated systems can perform and assess the feedback in a matter of minutes which enables testing of algorithms for controlling surgery, materials, etc.

It should be appreciated that certain aspects of the embodiments herein require software implemented with the computer system 100 as disclosed above. This software can incorporate machine learning, finite element analysis, machine vision, and overlay guiding systems. Machine learning can commence initially by assessing pictures of surgeries and correlating them with mechanical measurement data or simulation data from finite element analysis to determine what affects suture success for an artificial intelligence to then predict the next best step. Finite element analysis (FEA) requires external validation with mechanical testing and can operate by using machine vision to determine where sutures are and then model those with macros in a FEA environment that models stresses and then suggests the next surgical steps. Pattern recognition can be done by sensing colored sutures with machine vision and then determining mechanical outcomes with testing, FEA, or other means. The overlay guiding systems take input from the recommendations of the artificial intelligence or could be programmed by an instructor to then show the user where to place their next suture. This can be adaptive to place their next suture based on predictions of whether their current surgery is succeeding or not.

Figure 20A:
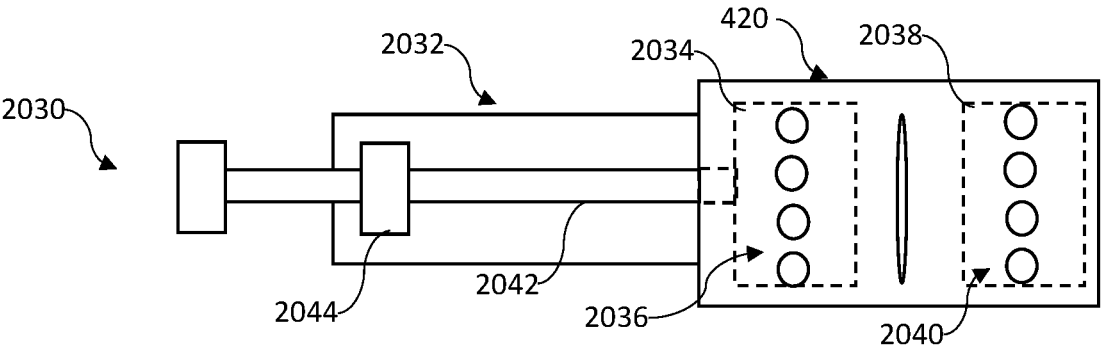
FIG. 20A depicts another manual biomaterial tensioning system, in accordance with the disclosed embodiments.
Figure 20B:
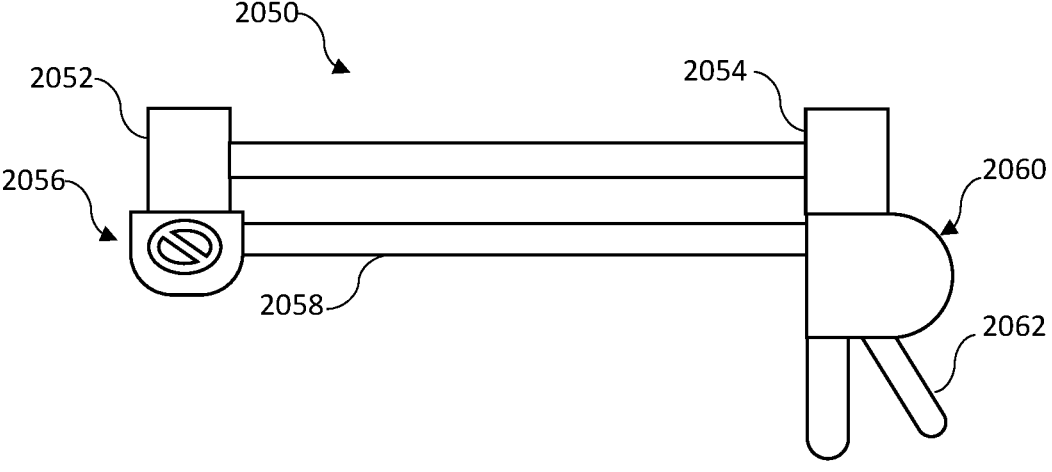
FIG. 20B depicts another manual biomaterial tensioning system, in accordance with the disclosed embodiments.

FIG. 20A and FIG. 20B illustrate exemplary embodiments of manual tensioning systems. FIG. 20A illustrates a top plan view of a single bolt tensioning system 2030 in accordance with the disclosed embodiments. The system 2030 includes a base holder 2032, connected to a slider 2034, with a plurality of posts 2036 thereon. The distal end of the base holder 2032 can include a block 2038 with a plurality of posts 2040. The system 2000 further includes a bolt 2042 operably connected to the slider 2034. A threaded mount 2044 extends from the base holder 2032, and allows the bolt 2042 to adjust the slider 2034 to impart tension on a biomaterial 420.

FIG. 20B illustrates an elevation view of a ratchet tensioning system 2050. The ratchet tensioning system. The ratch tensioning system includes a bracket mount 2052 and a second bracket mount 2054. The bracket mount 2052 is attached to an extendable end 2056 of a ratchet bar 2058. The end of the ratchet bar 2058 can be disengaged from a ratchet 2060. The ratchet 2060, includes an operable handle 2062 allowing the ratchet to incrementally extend or retract the ratchet bar 2058. The bracket mount 2052 and second bracket mount 2054 can each be used to hold a clamp, such as clamp 405, which can be used to hold a biomaterial.

Figure 21A:
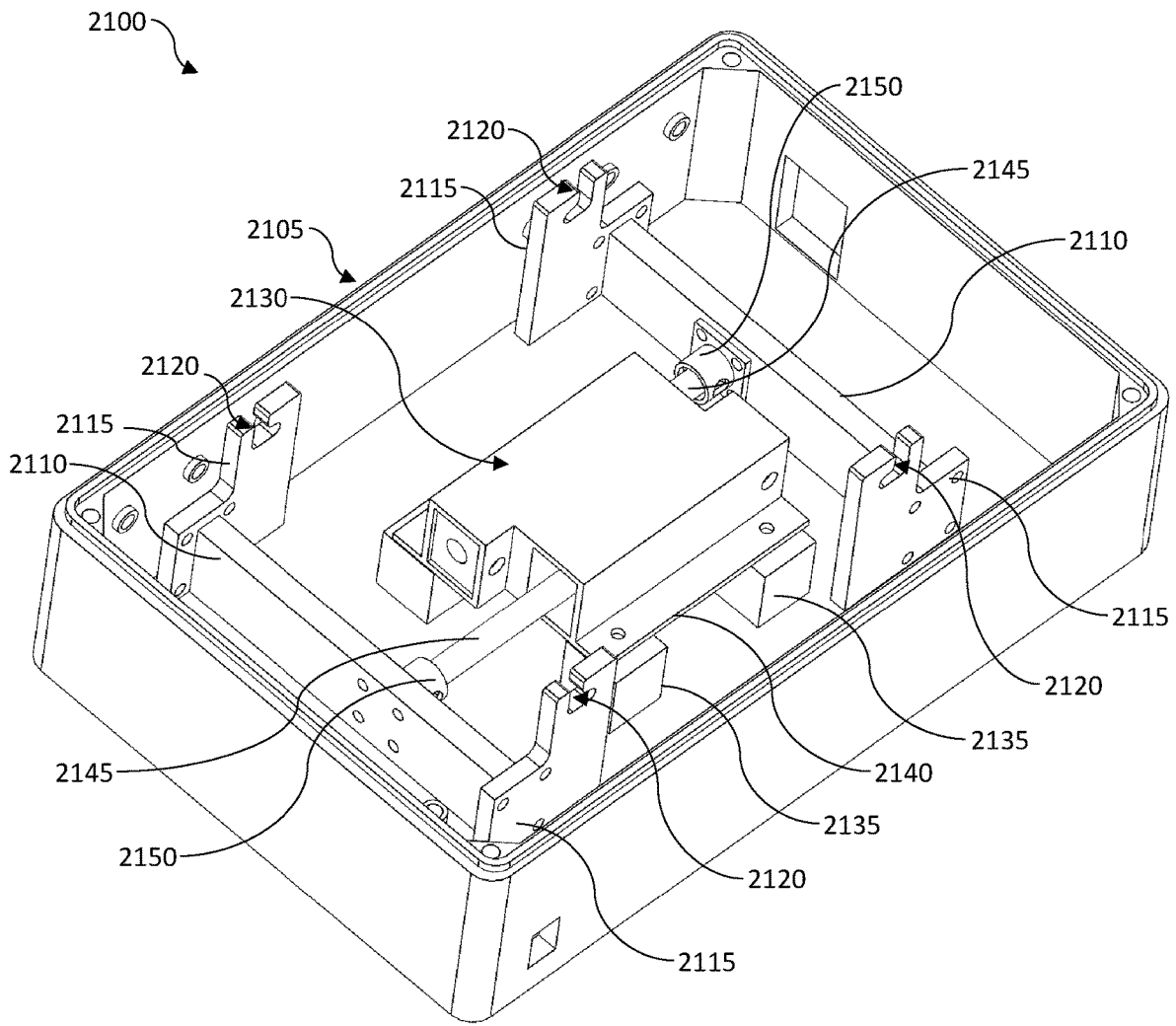
FIG. 21A depicts a linear actuated biomaterial tensioning system, in accordance with the disclosed embodiments.

FIG. 21A illustrates a surgical training system 2100 in accordance with the disclosed embodiments. The surgical training system 2100 comprises a housing 2105, fitted with slidable braces 2110. Each end of the slidable braces 2110 includes a riser 2115, with a cutout 2120. The cutout is configured with a narrow top opening and a lower slot configured to accept a bar 2125.

A linear actuator 2130 can be mounted in the middle of the housing 2105 on mounting blocks 2135 using mounting flange 2140. The linear actuator 2130 can drive linear extension and retraction of arms 2145. The arms 2145 can be operably connected to the slidable braces 2110 via mounting cuffs 2150.

Figure 21B:
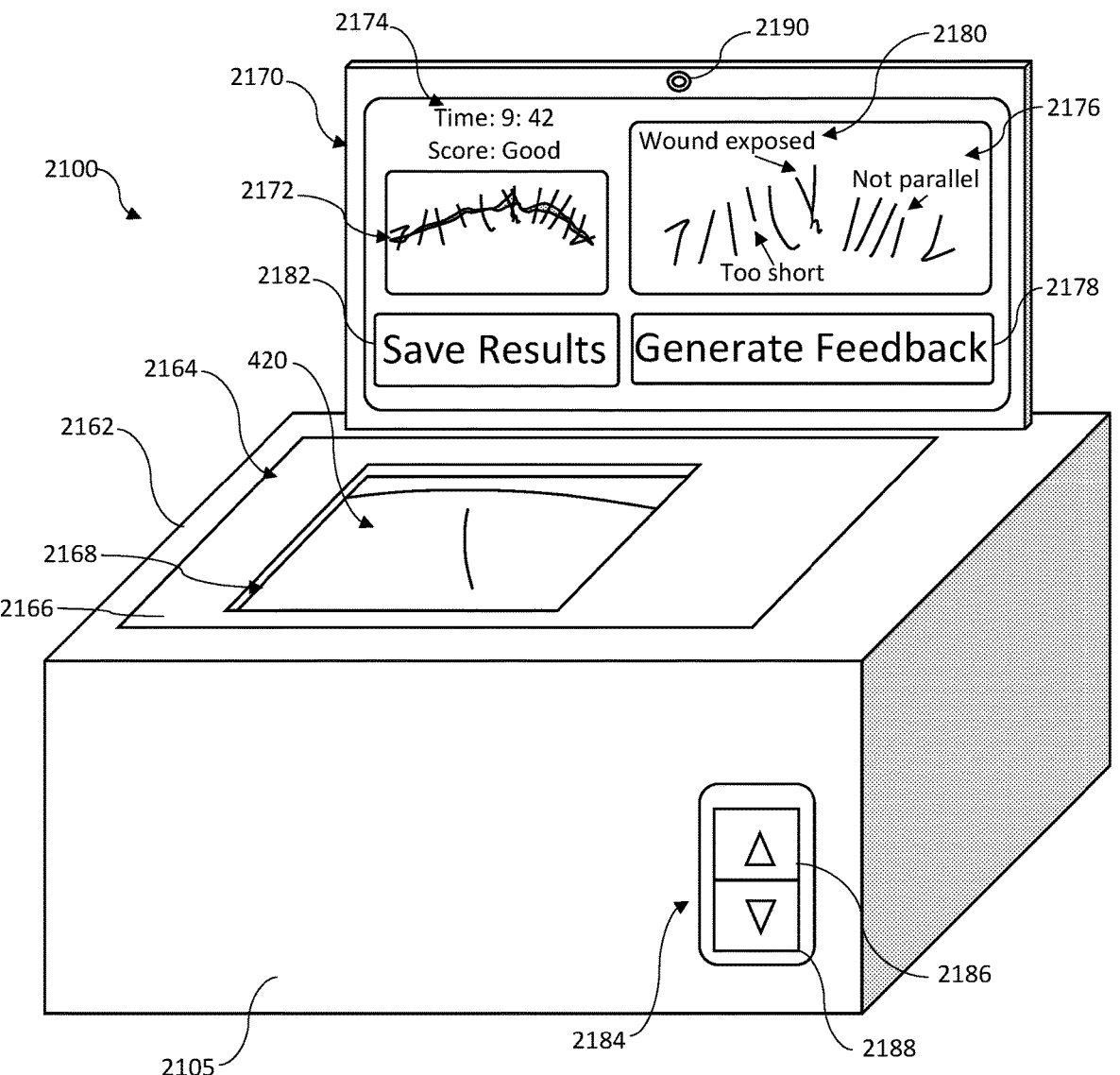
FIG. 21B depicts additional aspects of a linear actuated biomaterial tensioning system, in accordance with the disclosed embodiments.

FIG. 21B illustrates additional aspects of the surgical training system 2100, in accordance with the disclosed embodiments. The surgical training system 2100 can include a lib 2162 configured to enclose the top of the housing 2105. The lib 2162 can include a cutout 2164 with a sliding cover 2166. The sliding cover 2166 can further include a window 2168 which provides access to the biomaterial 420 under tension inside the housing 2105. The housing includes a button 2184, comprising a bi-directional button that can be operably connected to the linear actuator 2130. The top button 2186 can increase the tension and the bottom button 2188 can decrease the tension.

The surgical training system 2100 can further include a user interface 2170 and camera 2190. The interface 2170 can comprise a tablet computing device as described in FIGS. 1-3, with a touchscreen interface. The interface 2170 can include an image of the stitching 2172, along with details view 2174, which can include, for example, time taken suturing, and a rating of the suturing job. The interface 2170 can also include a rendering of the sutures 2176. The interface 2170 includes a feedback button 2178 which, when operated, can generate feedback 2180 on the completed suturing. The feedback can be based on a computer module configured to evaluate suturing with machine learning. Results of the suturing can be saved with a save button 2182, which allows the user to review previous efforts.

The interface 2170 enables users to watch educational modules, use assessment algorithms to rate their performance, and support machine learning assessment approaches. A machine vision detection system can assess in real-time how well suturing is being performed in terms of spacing and symmetry which will be combined with machine learning to suggest alternatives to common problems and guide users with a video overlay or augmented reality system. Aspects of the associated methods are illustrated in FIG. 19.

The system 2100 is built into a housing 2105 that allows modular placements of components underneath such as the patient body simulator 425. The patient body simulator 425 can also be configured to simulate suturing for different parts of the body, such as the head, arms or legs with appropriate biomaterials installed to represent the appropriate portion of the body. In certain embodiments, strain sensors or load cells can be formed directly in the biomaterial to measure the actuation force to provide quantitative feedback to the user.

Figure 21C:
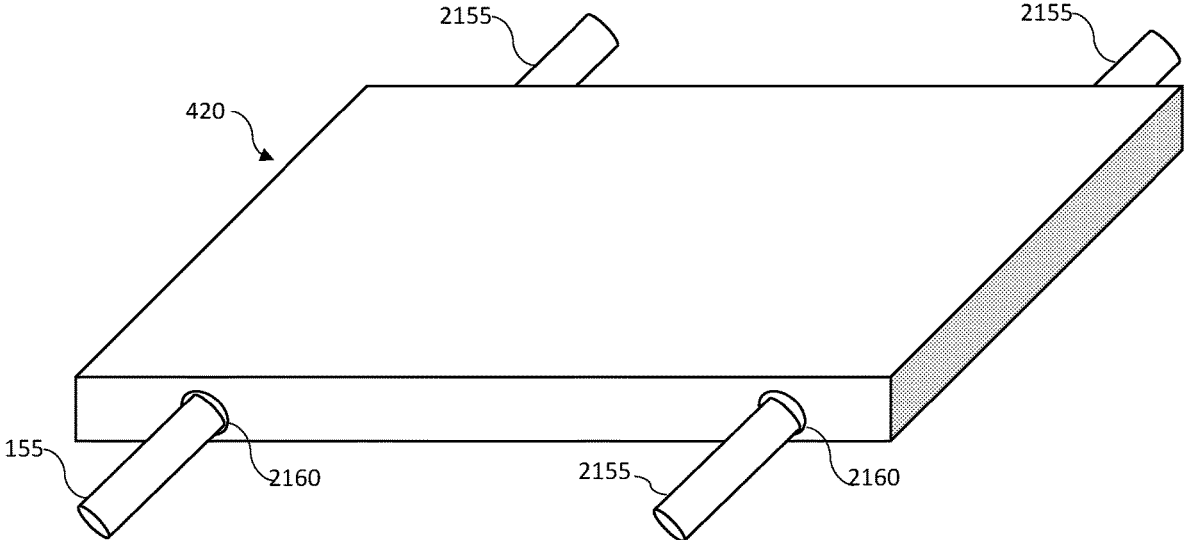
FIG. 21C depicts a biomaterial for a linear actuated biomaterial tensioning system, in accordance with the disclosed embodiments.

In operation, the linear actuator 2130 can be used to impart tension on a biomaterial 420. FIG. 21C illustrates a specially configured biomaterial 420 with rods 2155, which are passed through the biomaterial 420 in channels 2160. It should be appreciated that the channels can be cut into the biomaterial, or the rods 2155 can be built into the biomaterial as the biomaterial is fabricated. The rods 2155 are configured to fit into cutouts 2120 in the surgical training system 2100. The ends of the rods 2155 can be sized to fit into one of each of the respective cutouts 2120. Once the rods 2155 are installed the linear actuator can extend or retract the slidable braces 2110 in order to impart tension on the biomaterial 420.

It should be appreciated that the disclosed embodiments are intended for a number of use cases that dictate different detailed layouts. For instance, a smaller version systems could be implemented so sutures could be conducted on a handheld device and either tested with internal actuators or interfaced with the current actuation system which allows the user to practice suturing away from the main device. The system can be used without a physiological body or tray in order to use the actuators to test biomaterial strength or to test a completed by a machine, robot, or means other than user suturing. The device can also comprise a smaller version suitable for simpler testing, such as basic sutures for medical students that do not involve the complexity of the abdominal wall. Touch-screen interfaces, mechanical buttons/switches, augmented reality, and further interfaces could all be used to control the device. Remote and programmed control enable changing of device behavior by an instructor or according to a pre-specified routine that is challenging to the user.

It may be advantageous for trainees to view and interact with the underside of the biomaterials post-usage. Thus, incorporation of a flipping mechanism by which an axis centrally mounted through or near the suture biomaterials can allow the material to rotate 180 degrees by a pair of bearings mounted at each end of the axis, at the discretion of the user. This may be controlled manually or electronically. This 'flip' would expose the underside of the working medium for inspection, data collection, and further learning opportunity. It is also possible to have waterproof cameras integrated in the system that view the surgical operation from below.

Figure 22A:
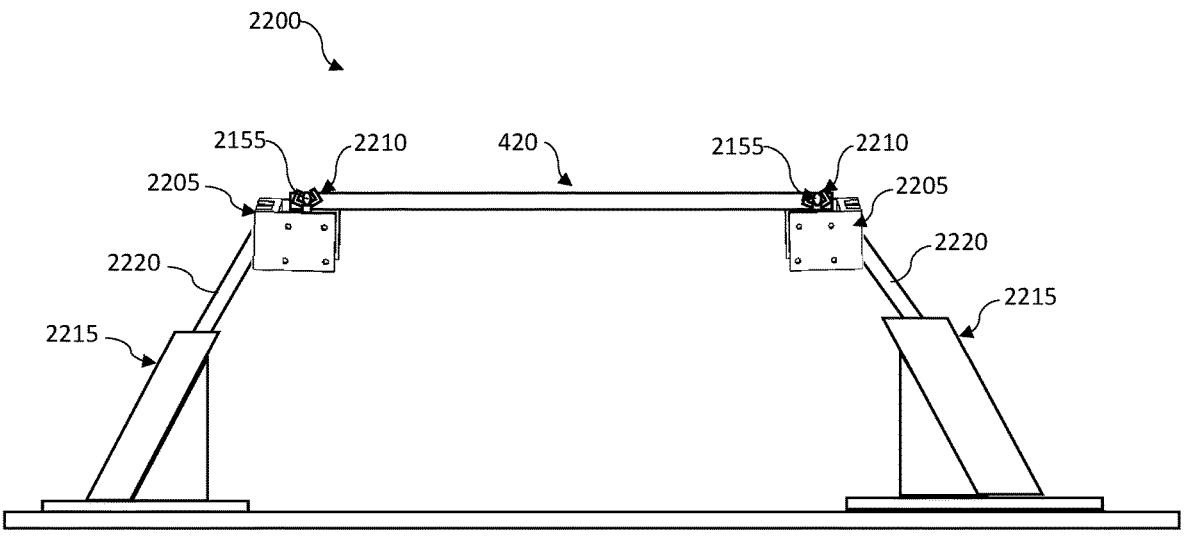
FIG. 22A depicts a clamp and lock surgical training system, in accordance with the disclosed embodiments.

FIG. 22A illustrates a clamp and lock surgical training system 2200 in accordance with the disclosed embodiments. The clamp and lock surgical training system comprises bar mounts 2205 configured to accept a rod 2155 in jaws 2210. The bar mounts can be mounted to a linear actuator 2215 which can be configured to extend or retract arm 2220.

In use, the clamp and lock surgical training system 2200 can be used to tension a biomaterial 420. The ends of rods 2155 in the biomaterial 420 can inserted into the jaws 2155 disposed on each end of the bar mounts. The bar mounts 2205 can be further configured to attach to the arms 2220. With the biomaterial 420 in place, the linear actuator 2215 can retract the arms 2220, thereby exerting tension on the biomaterial 420.

Figure 22B:
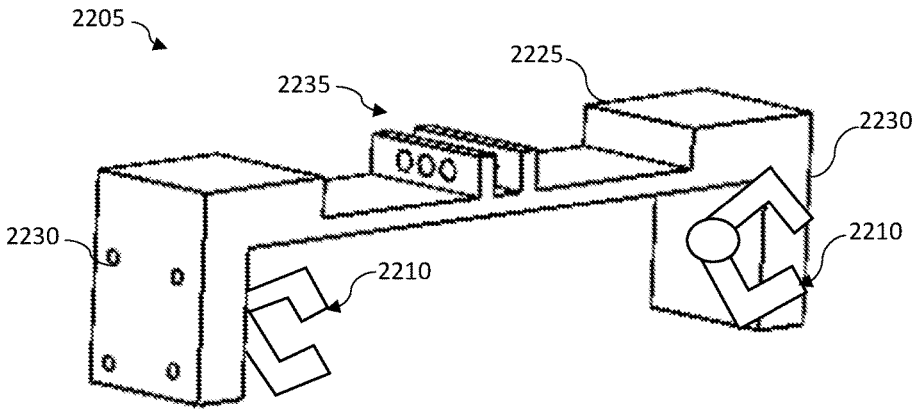
FIG. 22B depicts a bar mount for a clamp and lock surgical training system, in accordance with the disclosed embodiments.

Aspects of the bar mounts 2205 are illustrated in FIG. 22B. The bar mount 2205 comprises an a base 2225, with wings 2230. The wings 2230 are fitted with jaws 2210. The back side of the base 2225 further comprises an arm mount 2235, configured to allow the arm 2220 to engage the bar mount.

It should be appreciated that the disclosed embodiments recreate the complex abdominal wall that has layers of skin, muscle, fat, and fascia for the disclosed devices. The importance of these layers for training advanced surgical techniques that require suturing throughout the material layers and peeling between layers is noteworthy. The intestines/guts provide further realism that recreate the surgical environment and enables adjustable BMI of patient based on the thickness of fat in the biomaterial that presents a major challenge for surgeons.

Physiological functions such as bleeding/fluids are also incorporated in the disclosed embodiments with integrated breathing/coughing that can be controlled by a touch-screen interface that enables the recreation of patient behaviors in the operating room. The coughing can be accomplished with a repurposed ventilation system.

Likewise, the educational training techniques disclosed herein extends beyond the mechanics assessment. The surgical training system disclosed herein is designed with clamps and modular parts that enable users to change biomaterials and readjust the machine which is necessary in a classroom setting and for setting up surgical scenarios for patients of different BMIs quickly and reliably. The surgical trainer can include a touch-screen interface that may incorporate training and video sessions for the student. A machine vision detection system can assess in real-time how well suturing is being performed in terms of spacing and symmetry which can be combined with machine learning to suggest alternatives to common problems and guide users with a video overlay or augmented reality system.

The disclosed embodiments thus provide a high-value low cost solution that provide higher fidelity training. The embodiments provide mechanical feedback to test sutures after a user has closed a wound, thereby providing tangible mechanical feedback that provides the user a transformative educational experience not offered by any other existing solution. The embodiments also enable the simulation and testing of synthetic biomaterials representative of patients with varied BMI which is not currently addressed in the medical education industry, especially for high BMI patients.

Based on the foregoing, it can be appreciated that a number of embodiments, preferred and alternative, are disclosed herein. In an embodiment, a surgical trainer comprises a first clamp configured to engage a biomaterial, a second clamp configured to engage the biomaterial, and at least one actuator operably connected to at least one of the first clamp and the second clamp wherein the at least one actuator is configured to impart tension in the biomaterial.

In an embodiment, the at least one actuator further comprises a first actuator operably connected to the first clamp and a second actuator operably connected to the second clamp.

In an embodiment, the surgical trainer further comprises an articulating joint configured between the actuator and at least one of the first clamp and the second clamp, the articulating joint being configured to impart the tension in the biomaterial. In an embodiment, the surgical trainer further comprises an actuator controller configured to control the tension imparted on the biomaterial by the actuator operably connected to at least one of the first clamp and the second clamp.

In an embodiment, the surgical trainer further comprises a patient body simulator arranged under the biomaterial. In an embodiment, the patient body simulator further comprises at least one of a synthetic body organ, a synthetic bone, and a synthetic bodily fluid. In an embodiment, the biomaterial comprises layers, the layers further comprising at least one of: synthetic skin, synthetic fat, synthetic fascia, and synthetic muscle.

In an embodiment, each of the first clamp and the second clamp further comprise an upper bracket, at least one joining post formed in the upper bracket, a lower bracket, and at least one lower bracket guide hole configured to accept the at least one joining post.

In an embodiment, the surgical trainer further comprises a lever configured on the upper bracket, the lever being adapted to connect the actuator to at least one of the first clamp and the second clamp.

In an embodiment, the surgical trainer further comprises an imaging device, the imaging device configured to capture image data of the biomaterial. In an embodiment, the surgical trainer further comprises a computer system, said computer system comprising: at least one processor; and a computer-usable medium embodying computer program code, the computer-usable medium capable of communicating with the at least one processor, the computer program code comprising instructions executable by the at least one processor and configured for: accepting input of the image data from the imaging device and providing feedback associated with the image data of procedures performed on the biomaterial.

In an embodiment, a surgical training method comprises configuring a biomaterial, clamping the biomaterial with a first clamp, clamping the biomaterial with a second clamp, and imparting tension on the biomaterial with at least one actuator operably connected to at least one of the first clamp and the second clamp, wherein the biomaterial serves as a training medium for surgical procedures.

In an embodiment of the method, the at least one actuator further comprises a first actuator operably connected to the first clamp and a second actuator operably connected to the second clamp.

In an embodiment, the surgical training method further comprises configuring an articulating joint between the actuator and at least one of the first clamp and the second clamp, the articulating joint imparting the tension in the biomaterial. In an embodiment, the surgical training method further comprises controlling the tension imparted on the biomaterial with an actuator controller for the actuator operably connected to at least one of the first clamp and the second clamp.

In an embodiment, the biomaterial comprises layers, the layers further comprising at least one of: synthetic skin, synthetic fat, synthetic fascia, and synthetic muscle.

In an embodiment, the surgical training method further comprises capturing image data of the biomaterial with an imaging device. In an embodiment, the surgical training method further comprises accepting input of the image data from the imaging device and providing feedback associated with the image data of procedures performed on the biomaterial.

In another embodiment, a surgical training system comprises: a housing, a first slidable brace connected to a linear actuator, a second slidable brace connected to the linear actuator, a riser on each side of the first slidable brace, the riser comprising a cutout configured to accept a rod, and a riser on each side of the second slidable brace, the riser comprising a cutout configured to accept a rod. In an embodiment, the surgical training system further comprises a biomaterial and at least one rod configured to extend through the biomaterial.

It will be appreciated that variations of the above-disclosed and other features and functions, or alternatives thereof, may be desirably combined into many other different systems or applications. Also, it should be appreciated that various presently unforeseen or unanticipated alternatives, modifications, variations, or improvements therein may be subsequently made by those skilled in the art which are also intended to be encompassed by the following claims.

What is claimed is:

1. A surgical trainer comprising:
a first clamp configured to engage a biomaterial;
a second clamp configured to engage the biomaterial wherein each of the first clamp and the second clamp further comprise:
an upper bracket;
at least one joining post formed in the upper bracket;
a lower bracket; and
at least one lower bracket guide hole configured to accept the at least one joining post; and
at least one actuator operably connected to at least one of the first clamp and the second clamp wherein the at least one actuator is configured to impart tension in the biomaterial.

2. The surgical trainer of claim 1 wherein the at least one actuator further comprises:
a first actuator operably connected to the first clamp; and
a second actuator operably connected to the second clamp.

3. The surgical trainer of claim 1 further comprising:
an articulating joint configured between the actuator and at least one of the first clamp and the second clamp, the articulating joint being configured to impart the tension in the biomaterial.

4. The surgical trainer of claim 1 further comprising:
an actuator controller configured to control the tension imparted on the biomaterial by the actuator operably connected to at least one of the first clamp and the second clamp.

5. The surgical trainer of claim 1 further comprising:
a patient body simulator arranged under the biomaterial.

6. The surgical trainer of claim 1 wherein the patient body simulator further comprises at least one of:
a synthetic body organ;
a synthetic bone; and
a synthetic bodily fluid.

7. The surgical trainer of claim 1 wherein the biomaterial comprises layers, the layers further comprising at least one of:
synthetic skin;
synthetic fat;
synthetic fascia; and
synthetic muscle.

8. The surgical trainer of claim 1 further comprising:
a lever configured on the upper bracket, the lever being adapted to connect the actuator to at least one of the first clamp and the second clamp.

9. The surgical trainer of claim 1 further comprising:
an imaging device, the imaging device configured to capture image data of the biomaterial.

10. The surgical trainer of claim 9 further comprising:
a computer system, said computer system comprising:
at least one processor; and
a computer-usable medium embodying computer program code, the computer-usable medium capable of communicating with the at least one processor, the computer program code comprising instructions executable by the at least one processor and configured for:
accepting input of the image data from the imaging device; and
providing feedback associated with the image data of procedures performed on the biomaterial.

11. A surgical training system comprising:
a housing;
a first slidable brace connected to a linear actuator;
a second slidable brace connected to the linear actuator;
a riser on each side of the first slidable brace, the riser comprising a cutout configured to accept a rod; and
a riser on each side of the second slidable brace, the riser comprising a cutout configured to accept a rod.

12. The surgical training system of claim 11 further comprising:
a biomaterial; and
at least one rod configured to extend through the biomaterial.

13. The surgical trainer of claim 11 further comprising:
a computer system, said computer system comprising:
at least one processor; and
a computer-usable medium embodying computer program code, the computer-usable medium capable of communicating with the at least one processor, the computer program code comprising instructions executable by the at least one processor and configured for:
accepting input of the image data from an imaging device; and
providing feedback associated with the image data of procedures performed on the biomaterial.

* * * * *